US012594011B2

(12) United States Patent
Puttananjegowda et al.

(10) Patent No.: US 12,594,011 B2
(45) **Date of Patent: *Apr. 7, 2026**

(54) CMOS-BASED LOW-POWER, LOW-NOISE POTENTIOSTAT CIRCUIT AND ITS INTEGRATION WITH AN ENFM-BASED GLUCOSE SENSOR

(71) Applicant: UNIVERSITY OF SOUTH FLORIDA, Tampa, FL (US)

(72) Inventors: Kavyashree Puttananjegowda, Tampa, FL (US); Sylvia Thomas, Orlando, FL (US); Arash Takshi, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 544 days.

This patent is subject to a terminal disclaimer.

(21) Appl. No.: 18/164,525

(22) Filed: Feb. 3, 2023

(65) Prior Publication Data

US 2023/0172495 A1 Jun. 8, 2023

Related U.S. Application Data

(63) Continuation of application No. 17/076,637, filed on Oct. 21, 2020, now Pat. No. 11,571,148.

(60) Provisional application No. 62/944,730, filed on Dec. 6, 2019, provisional application No. 62/927,227, filed on Oct. 29, 2019.

(51) Int. Cl.

| | |
|---|---|
| ***A61B 5/145*** | (2006.01) |
| ***A61B 5/00*** | (2006.01) |
| ***A61B 5/1468*** | (2006.01) |
| ***A61B 5/1486*** | (2006.01) |
| ***C12Q 1/00*** | (2006.01) |
| ***G01N 27/327*** | (2006.01) |

(52) U.S. Cl.

CPC ........ *A61B 5/14532* (2013.01); *A61B 5/1468* (2013.01); *A61B 5/1486* (2013.01); *A61B 5/72* (2013.01); *C12Q 1/002* (2013.01); *C12Q 1/006* (2013.01); *G01N 27/3271* (2013.01); *A61B 2560/0204* (2013.01); *A61B 2562/0285* (2013.01); *A61B 2562/125* (2013.01); *G01N 2333/904* (2013.01)

(58) Field of Classification Search

CPC ........ C12Q 1/001; C12Q 1/002; C12Q 1/006; G01N 27/3271; C12N 11/06-12; C12N 9/0006; C12Y 101/03004

See application file for complete search history.

(56) References Cited

U.S. PATENT DOCUMENTS

| | | | |
|---|---|---|---|
| RE44,695 | E | 1/2014 | Simpson et al. |
| 11,571,148 | B1 | 2/2023 | Puttananjegowda et al. |
| 2011/0129593 | A1 | 6/2011 | Lee et al. |
| 2016/0153025 | A1 | 6/2016 | Wu et al. |

FOREIGN PATENT DOCUMENTS

| | | |
|---|---|---|
| WO | 2001033207 A1 | 5/2001 |
| WO | 2012018777 A1 | 2/2012 |

OTHER PUBLICATIONS

Kavyashree Puttananjegowda Electrospun Nanofifibrous Membrane Based Glucose Sensor with Integration of Potentiostat Circuit Univ. of Southern Florida Thesis Jun. 2020, 113 pages, https://digitalcommons.usf.edu/etd/8986 (Year: 2020).

Ahmad, et al. "A Single ZnO Nanofiber-Based Highly Sensitive Amperometric Glucose Biosensor" J. Phys. Chem. C 2010, 114, 9308-9313.

Majidzadeh, et al. "Energy efficient low-noise neural recording amplifier with enhanced noise efficiency factor" IEEE Trans Biomed Circuits Syst. Jun. 2011;5(3):262-71.

*Primary Examiner* — Thane Underdahl
(74) *Attorney, Agent, or Firm* — HUSCH BLACKWELL LLP

(57) ABSTRACT

The present disclosure presents glucose sensing methods and systems. One such system comprises an electrospun-nanofibrous-membrane (ENFM)-based amperometric glucose sensor integrated on a silicon chip, in which the glucose sensor has a working electrode, a reference electrode, and a counter electrode, wherein the working electrode comprises an ENFM-based sensing electrode. The system further comprises a potentiostat circuit integrated on the silicon chip such that the potentiostat circuit comprises a voltage control unit to control a voltage difference between the working electrode and the reference electrode and a transimpedance amplifier to measure a current flow between the working electrode and the counter electrode, in which a strength of the current flow corresponds to an amount of glucose present in a sample of blood on the glucose sensor.

20 Claims, 21 Drawing Sheets

CMOS-BASED LOW-POWER, LOW-NOISE POTENTIOSTAT CIRCUIT AND ITS INTEGRATION WITH AN ENFM-BASED GLUCOSE SENSOR

CROSS-REFERENCE TO RELATED APPLICATION

This application is a continuation of U.S. patent application Ser. No. 17/076,637, filed Oct. 21, 2020, now U.S. Pat. No. 11,571,148, granted Feb. 7, 2023, which claims priority to U.S. provisional application entitled, "A CMOS-BASED LOW-POWER, LOW-NOISE POTENTIOSTAT CIRCUIT AND ITS INTEGRATION WITH AN ENFM-BASED GLUCOSE SENSOR," having Ser. No. 62/944,730, filed Dec. 6, 2019, and U.S. provisional application entitled, "A CMOS-BASED LOW-POWER, LOW-NOISE POTENTIOSTAT CIRCUIT AND ITS INTEGRATION WITH AN ENFM-BASED GLUCOSE SENSOR," having Ser. No. 62/927,227, filed Oct. 29, 2019, each of which are entirely incorporated herein by reference.

BACKGROUND

Diabetes has an impact on populations around the world and is currently cited as a public health epidemic. Being one of the leading causes of health disparities, disabilities, and death, diabetes is a disease triggered by high glucose levels in the blood, which may arise due to insufficient production of insulin. When unmonitored over time, diabetes can lead to severe health issues, such as blindness, organ failure (e.g. kidney, heart), and gangrene and subsequent amputation. To assist in the prevention of these long term complications, the Diabetes Care and Complications Trial (DCCT) suggests continuous monitoring of blood glucose and insulin levels could be key.

Such a continuous glucose monitoring system needs to be power efficient, compact, portable, sensitive, and have a linear response for targeted levels. Electrochemical enzymatic biosensors have become popular for point-of-care monitoring of glucose levels in the blood. The sensitivity of these biosensors can be significantly enhanced by the utilization of nanostructures in sensor fabrication. More specifically, an electrospun-nanofibrous-membrane (ENFM) can increase detection, sensitivity, provide larger surface-to-volume catalyst loading, and create a platform for effective enzyme binding. ENFMs are easily fabricated, cost effective, and can be tailored to detect a wide range of biochemical reactions with the appropriate materials and functionalization.

Potentiostats are generally used for electrochemical analysis such as chronoamperometry, cyclic voltammetry, and impedance spectroscopy and are a popular choice of measurement in amperometric biosensors. A general design for applying constant voltages and measuring a current in an electrochemical cell requires both positive and negative power supplies for the circuits. Some designs have sacrificed the exact potential that has to be appeared between the working and reference electrodes for the operation of the circuit with a single supply. Many enzyme functionalized working electrodes must maintain a negative potential with respect to the reference electrode. This limits the use of grounded counter electrode potentiostats in amperometric glucose sensors.

A potentiostat circuit required for three electrode electrochemical sensors has two parts, a voltage control unit (VCU) and a transimpedance amplifier (TIA). Different configurations may be used to design the TIA, one of which is an instrumentation amplifier. This instrumentation amplifier uses a large number of components generating high noise making it difficult to measure a low current level. A switched capacitor configuration in a more complex TIA helps to overcome the thermal noise in the feedback resistance, but the substrate noise due to digital switching remains an issue for output linearity. Furthermore, when using a current mirror configuration in a TIA design for biosensing, a single-ended output is used to control the cell potential, which limits the current measurement in only one direction and causes nonlinearity at high current levels. With recent advancements in the bioelectronics arena, increasing demand for power reduction in potentiostats has presented a challenge to the industry. In a robust integrated circuitry, very low-power consumption, and low-noise performance is essential.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Figure 1A:
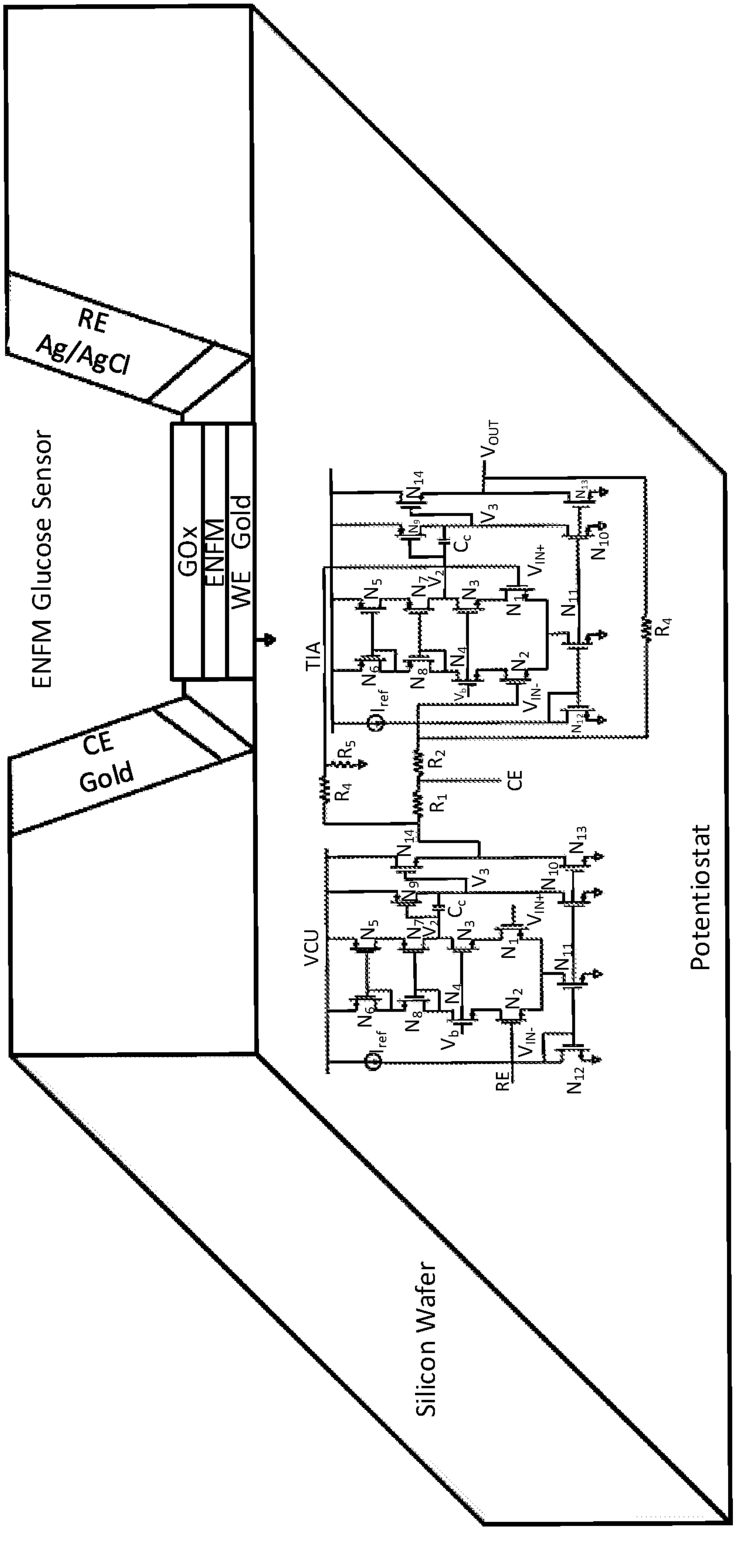
FIG. 1A is a diagram of a first electrochemical ENFM-based glucose sensor integrated with a CMOS potentiostat on a single silicon chip in accordance with various embodiments of the present disclosure.
Figure 1B:
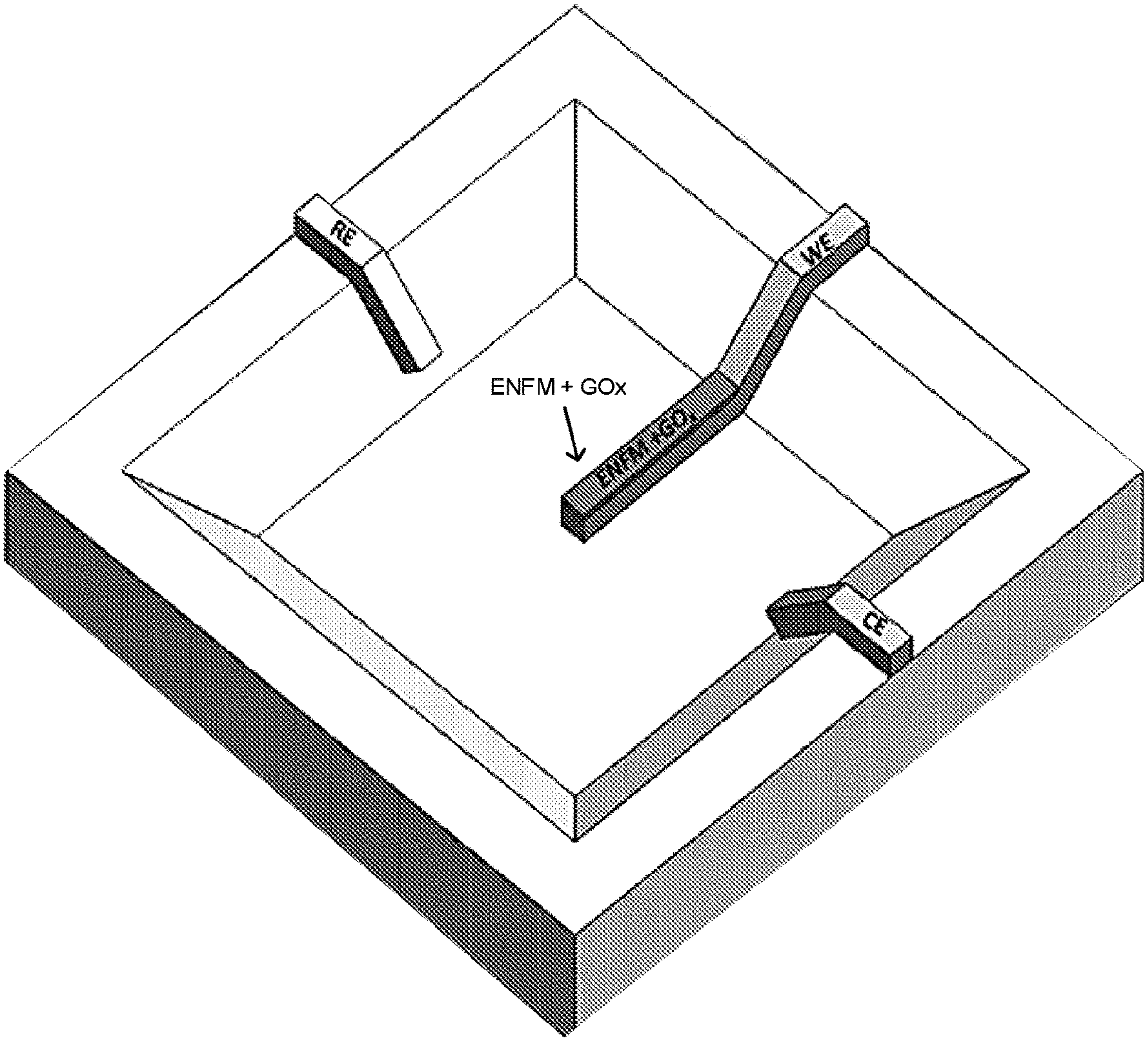
FIG. 1B is a top-view diagram of the first electrochemical ENFM-based glucose sensor of FIG. 1A.
Figure 1C:
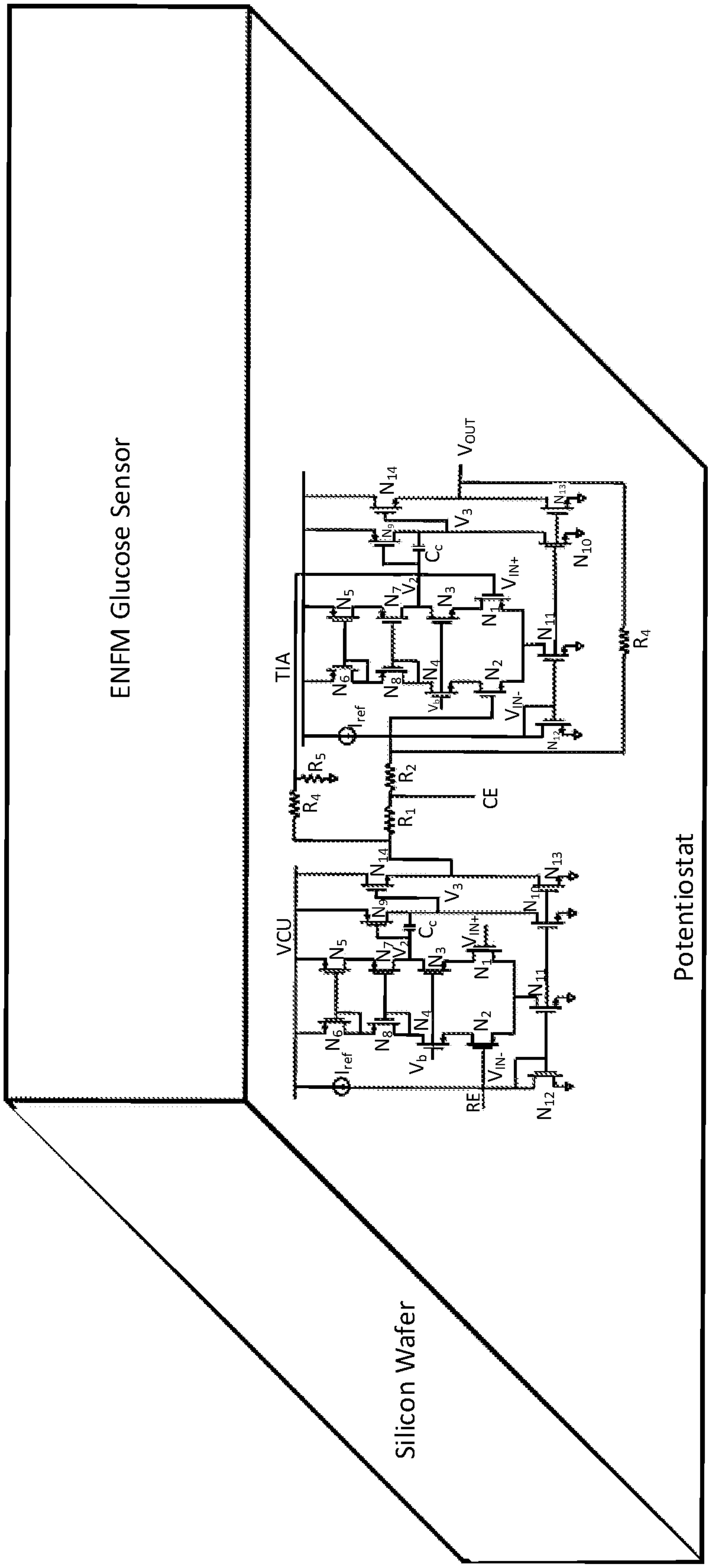

FIC. 1C is a bottom-view diagram of the first electrochemical ENFM-based glucose sensor of FIG. 1A.

Figure 1D:
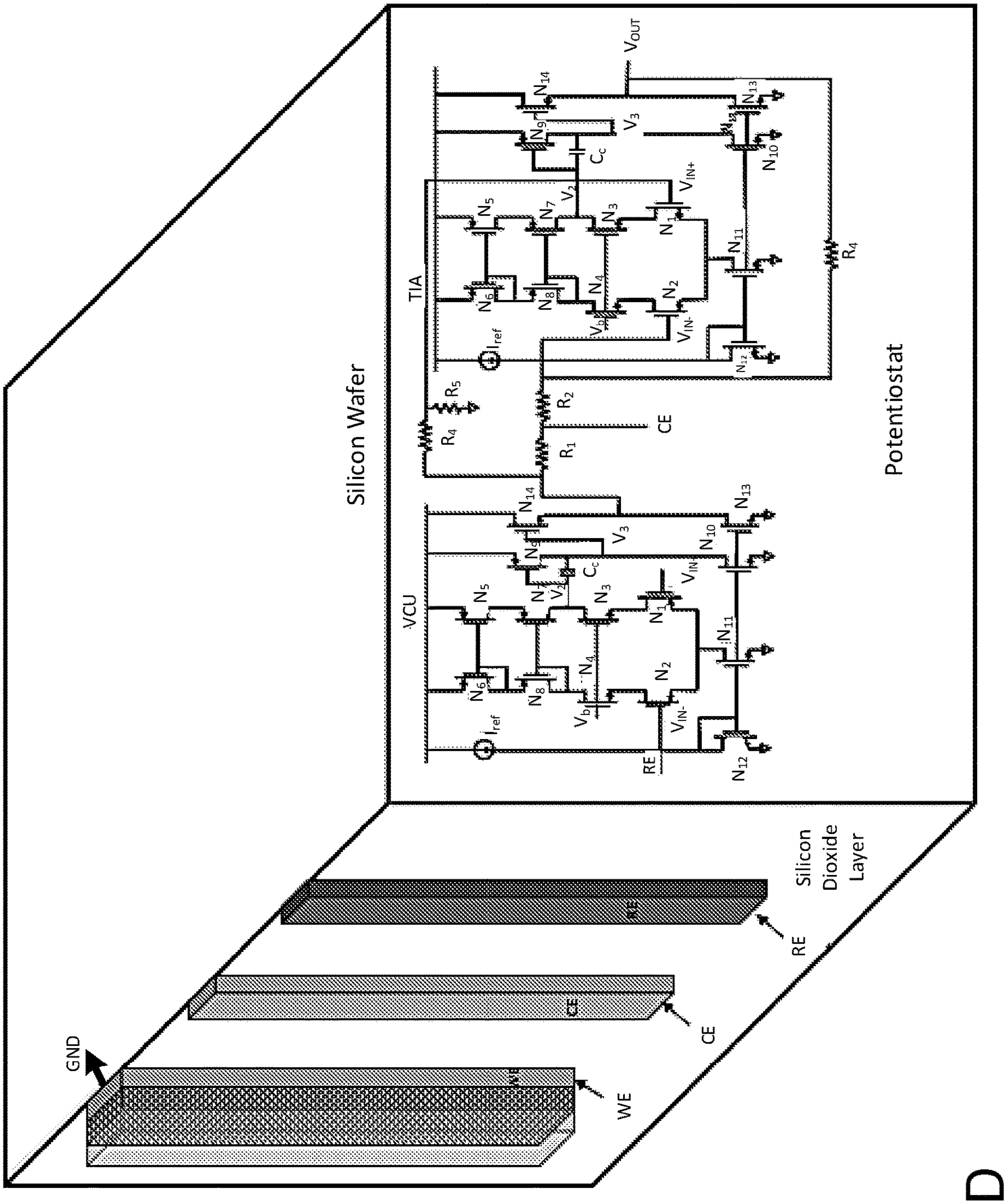

FIG. 1D is a second electrochemical ENFM-based glucose sensor integrated with a CMOS potentiostat on a single silicon chip in accordance with various embodiments of the present disclosure.

Figure 1E:
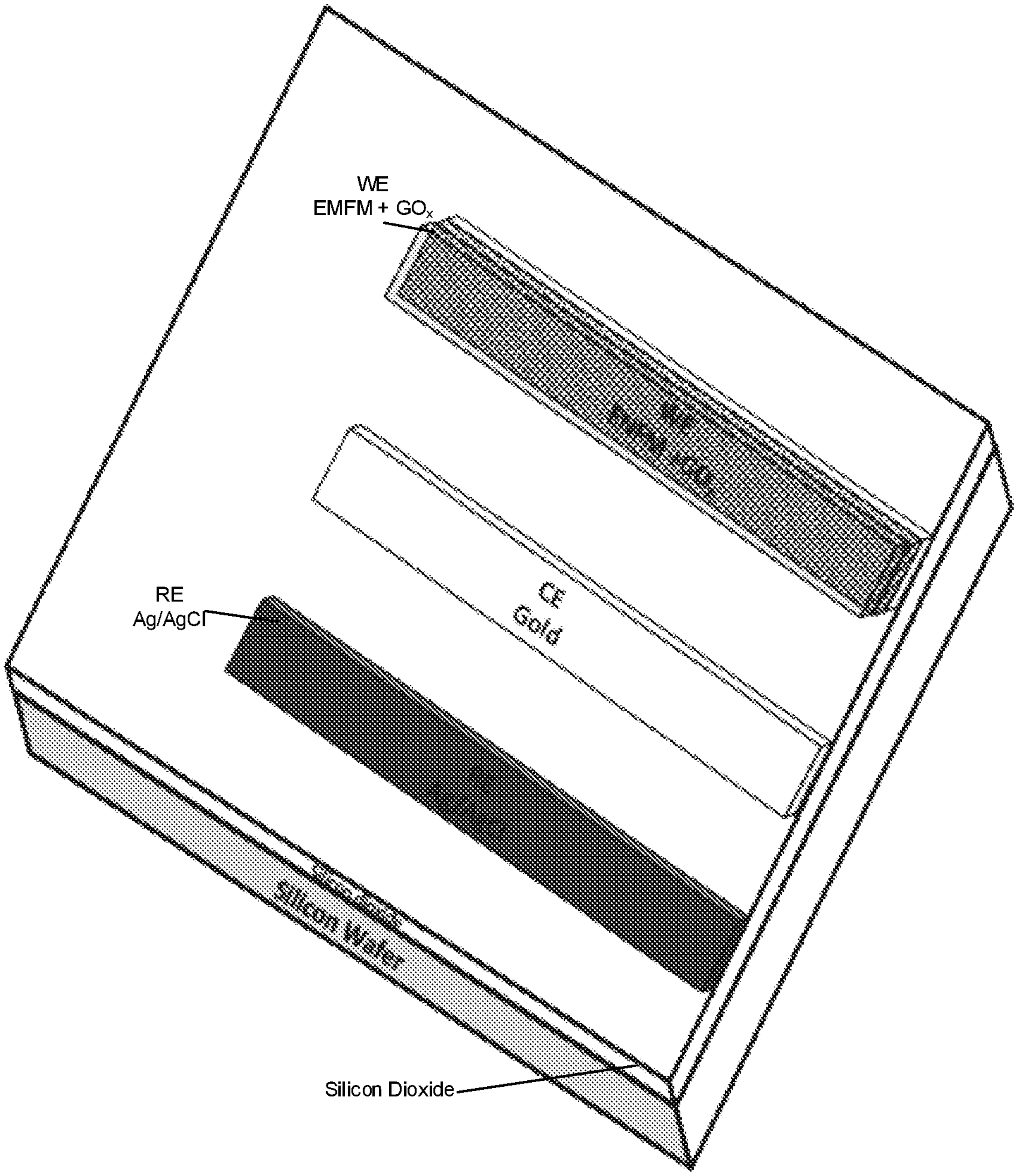
Figure 1F:
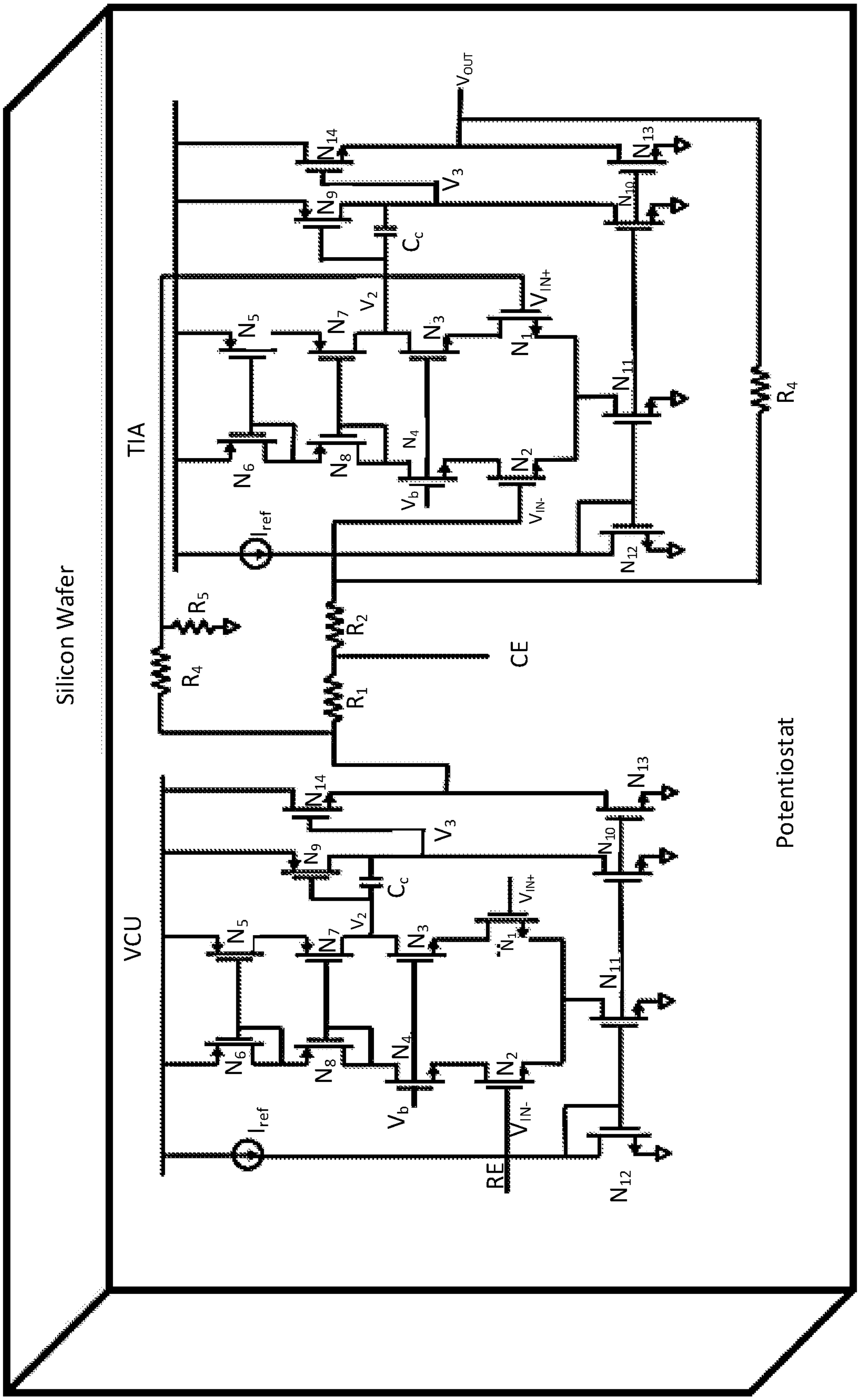

FIG. 1E is a top-view diagram of the second electrochemical ENFM-based glucose sensor of FIG. 1A.

FIC. 1F is a bottom-view diagram of the second electrochemical ENFM-based glucose sensor of FIG. 1A.

FIGS. 2A-2D show an exemplary first fabrication process of an ENFM-based electrochemical glucose sensor on a silicon chip in accordance with various embodiments of the present disclosure.

FIGS. 2E-2H show an exemplary second fabrication process of an ENFM-based electrochemical glucose sensor on a silicon chip in accordance with various embodiments of the present disclosure.

FIGS. 3A-3F show scanning electron microscope (SEM), transmission electron microscope (TEM), and atomic force microscope (AFM) images of a fabricated ENFM-based glucose sensing electrode in accordance with embodiments of the present disclosure.

Figure 4:
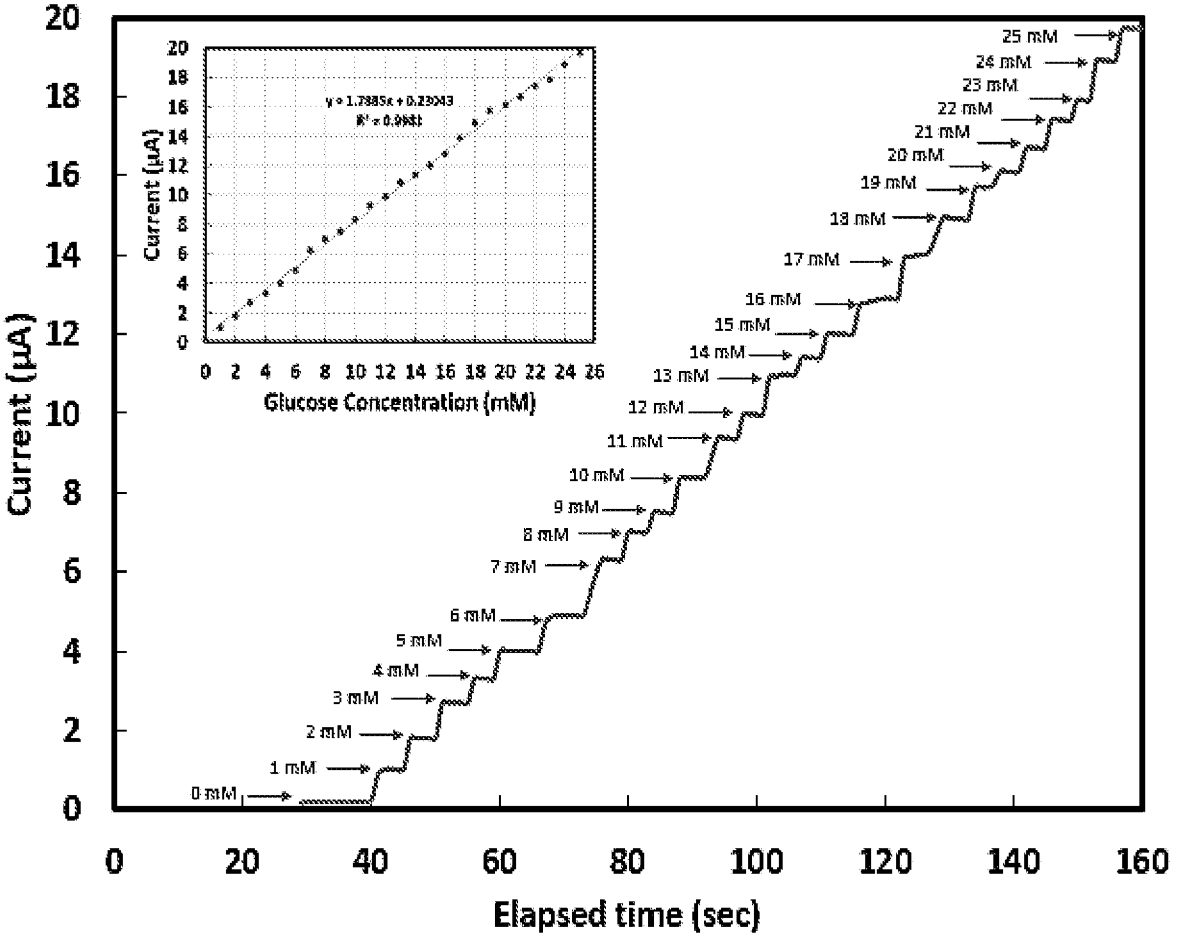

FIG. 4 is a diagram showing electrocatalytic activity of a working electrode in an exemplary ENFM-based glucose sensor using chronoamperometry for a successive increase of glucose concentration in accordance with embodiments of the present disclosure.

Figure 5:
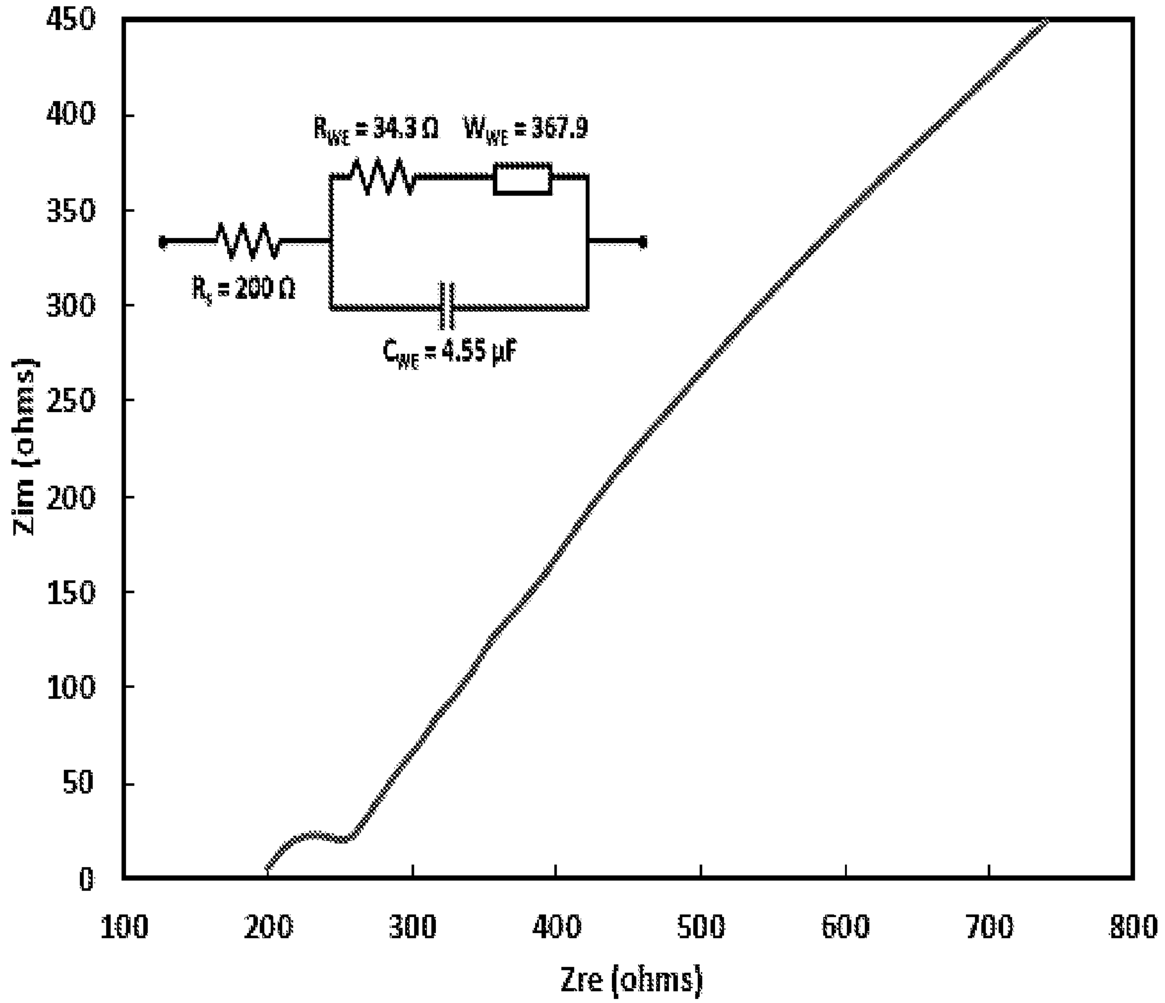

FIG. 5 is a diagram showing a Nyquist plot and an equivalent circuit model of an exemplary ENFM-based glucose sensing electrode with a 5 mM glucose concentration within a frequency ranges from 100 mHz to 10 KHz at an amplitude of 10 mV in accordance with embodiments of the present disclosure.

Figure 6:
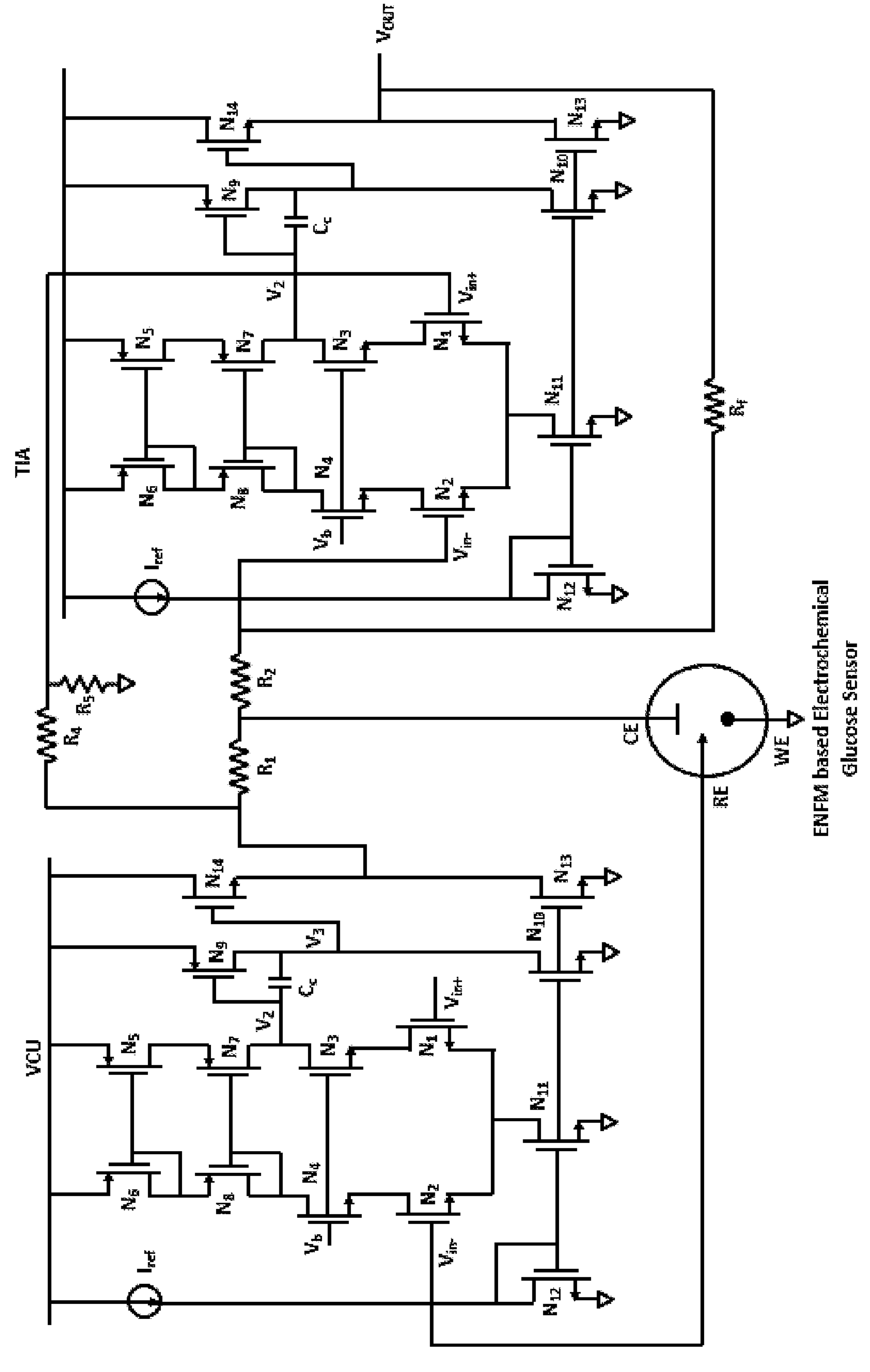

FIG. 6 is a diagram shown an electrochemical ENFM-based glucose sensor with an integrated potentiostat circuit design in accordance with embodiments of the present disclosure.

Figure 7:
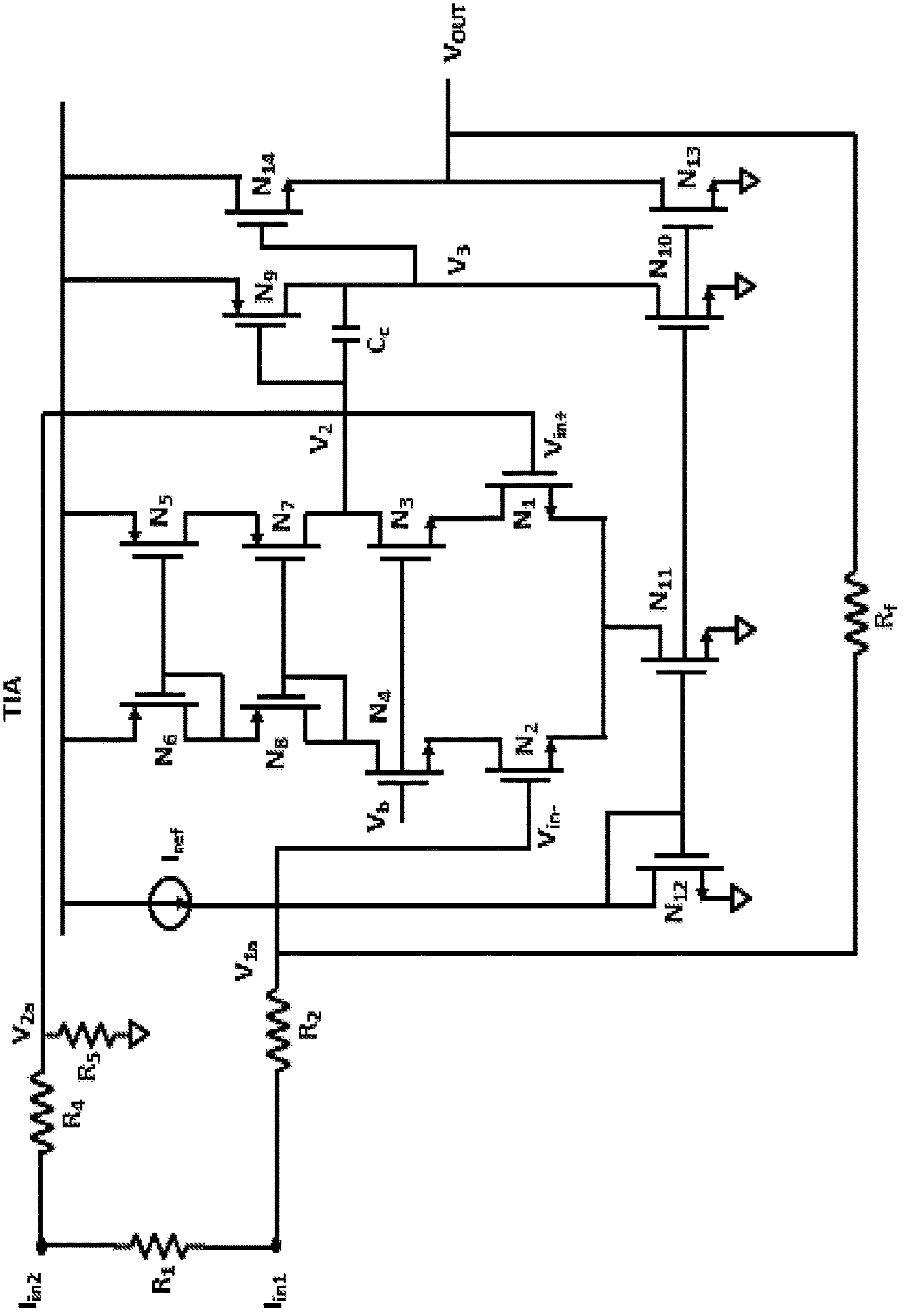

FIG. 7 shows an exemplary difference-differential telescopic cascode amplifier circuit utilized in the potentiostat circuit design of FIG. 6 in accordance with embodiments of the present disclosure.

Figure 8:
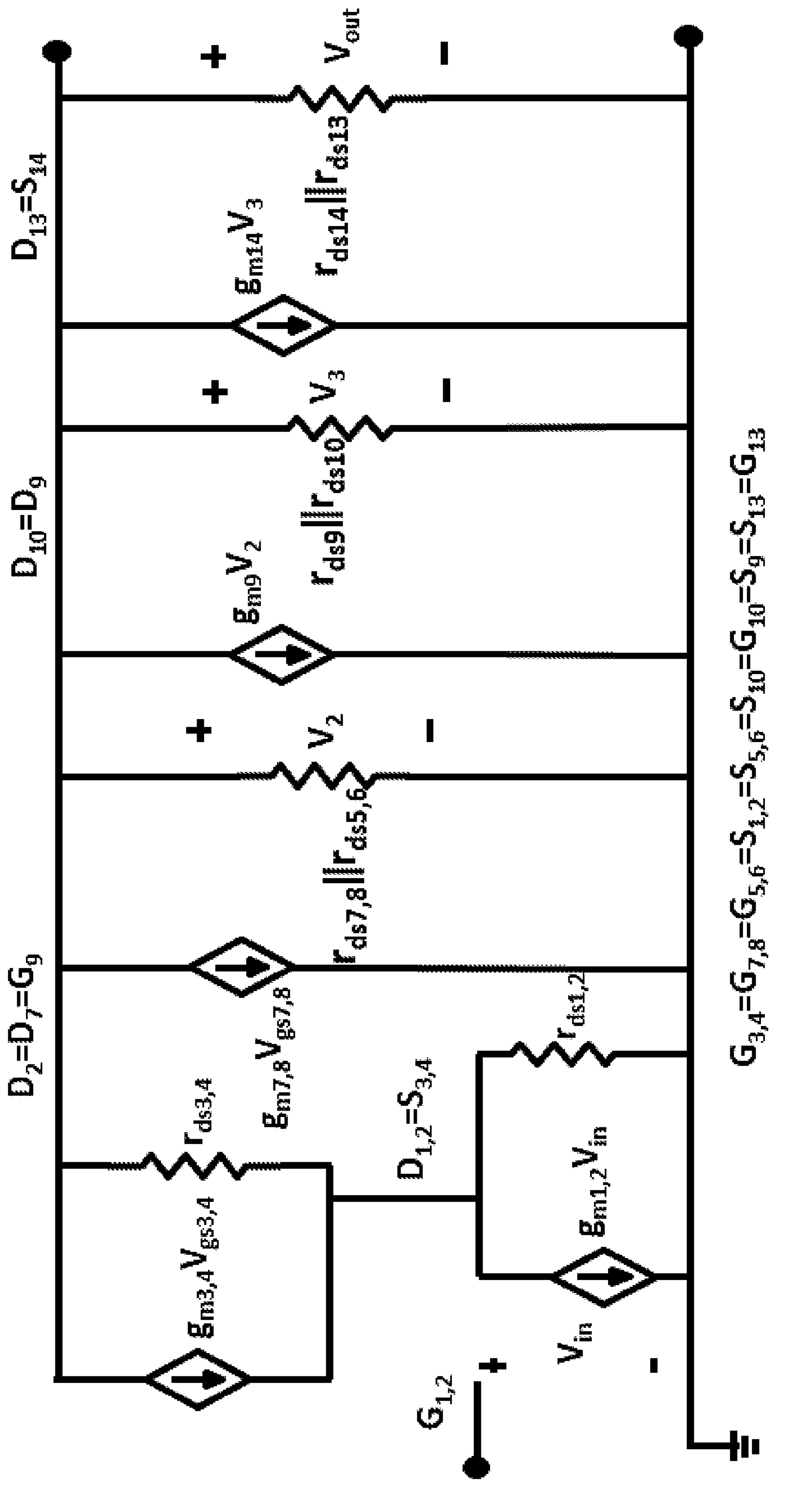

FIG. 8 shows a small signal analysis of the difference-differential telescopic cascode amplifier of FIG. 7.

Figure 9:
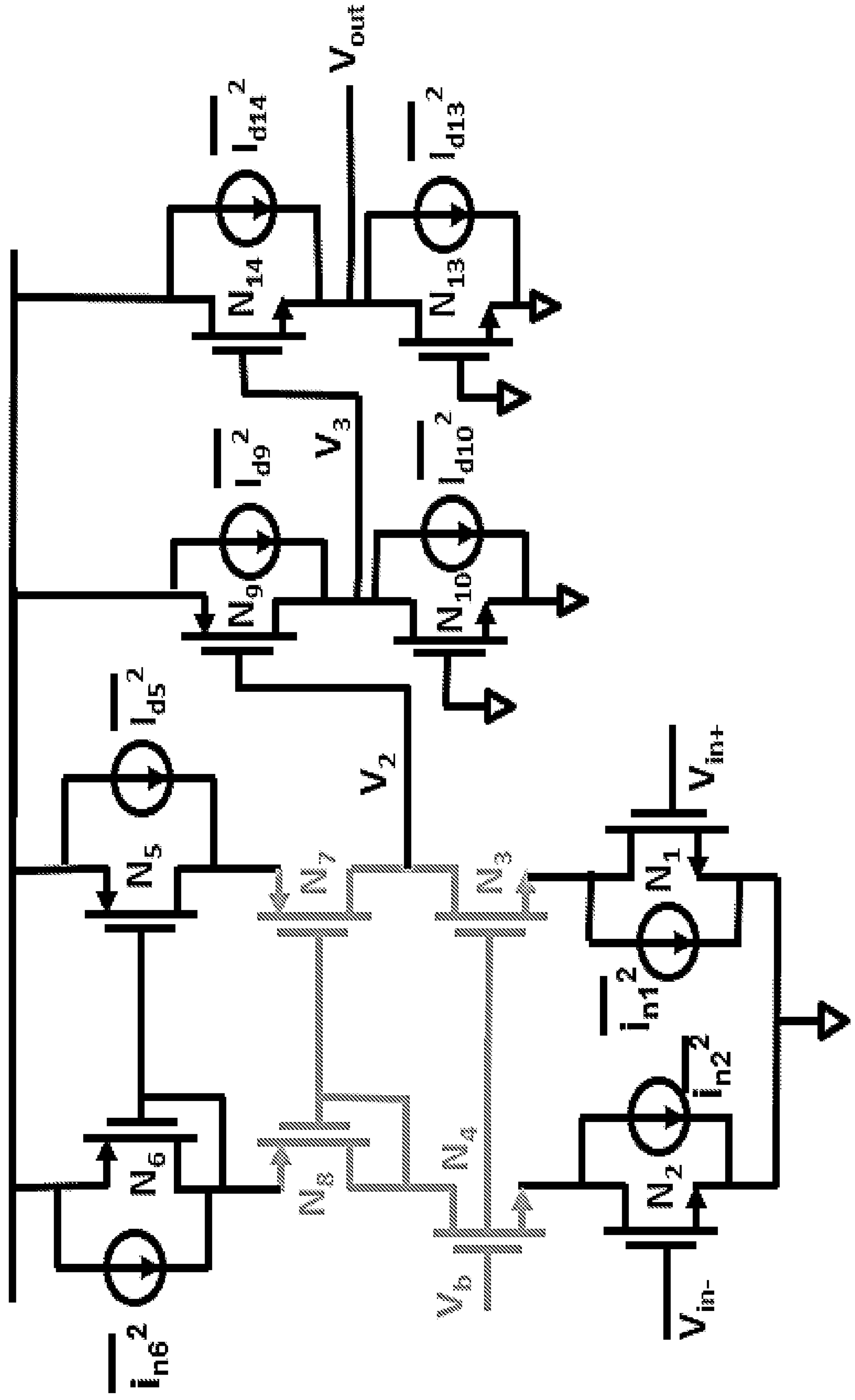

FIG. 9 shows a noise analysis of an exemplary difference-differential telescopic cascode amplifier of FIG. 7.

Figure 10A:
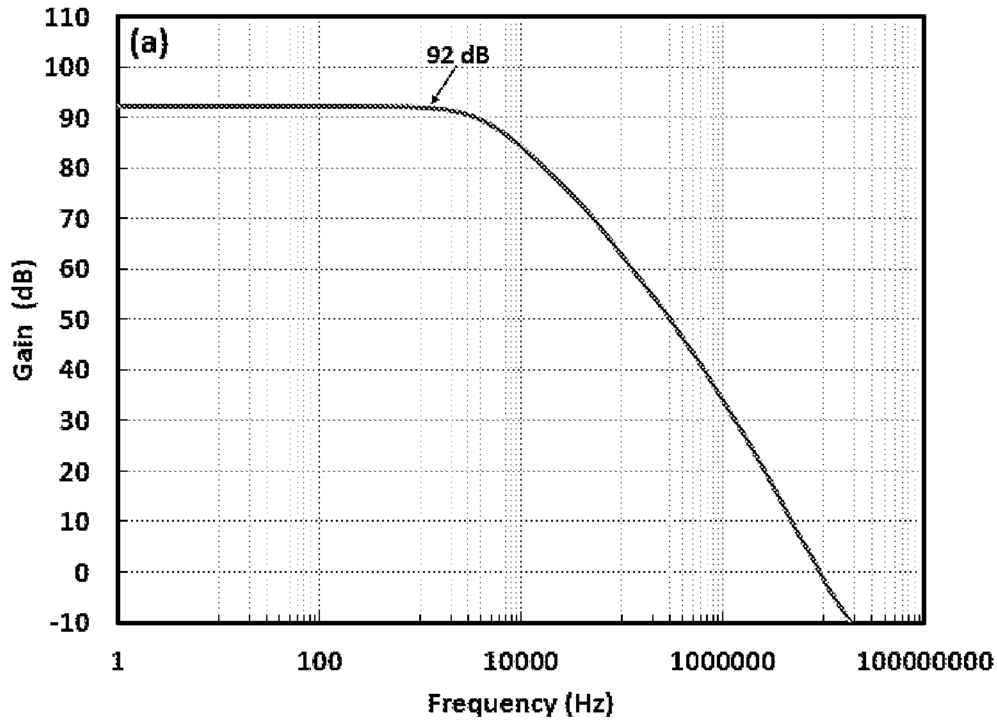
Figure 10B:
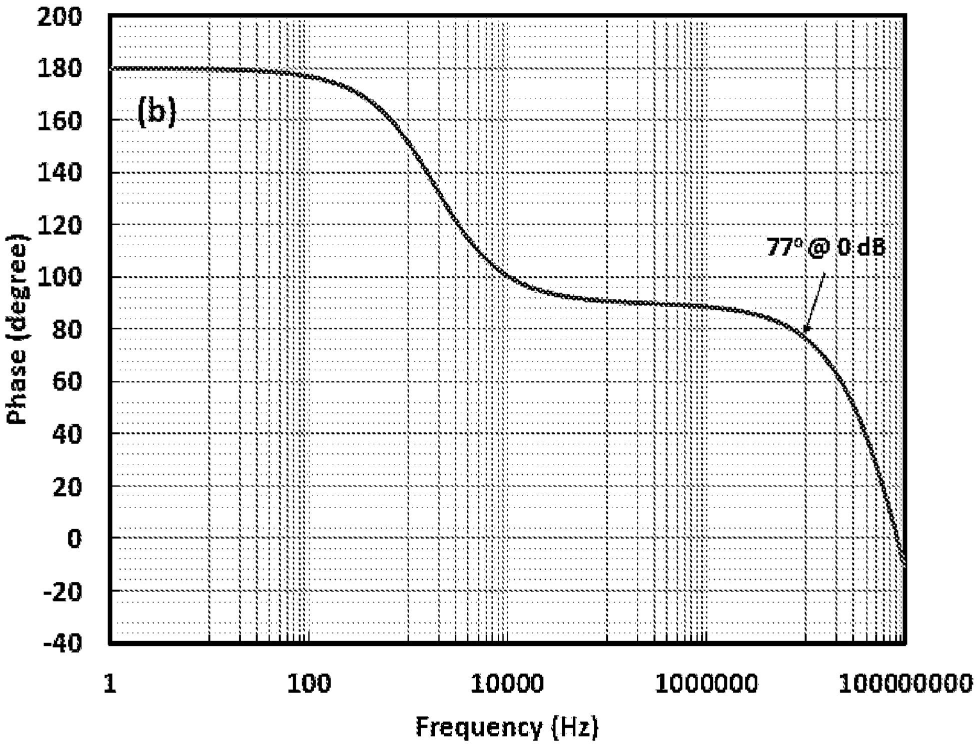

FIGS. 10A-10B show an open loop gain and a phase response of the difference-differential telescopic cascode amplifier of FIG. 7.

Figure 11:
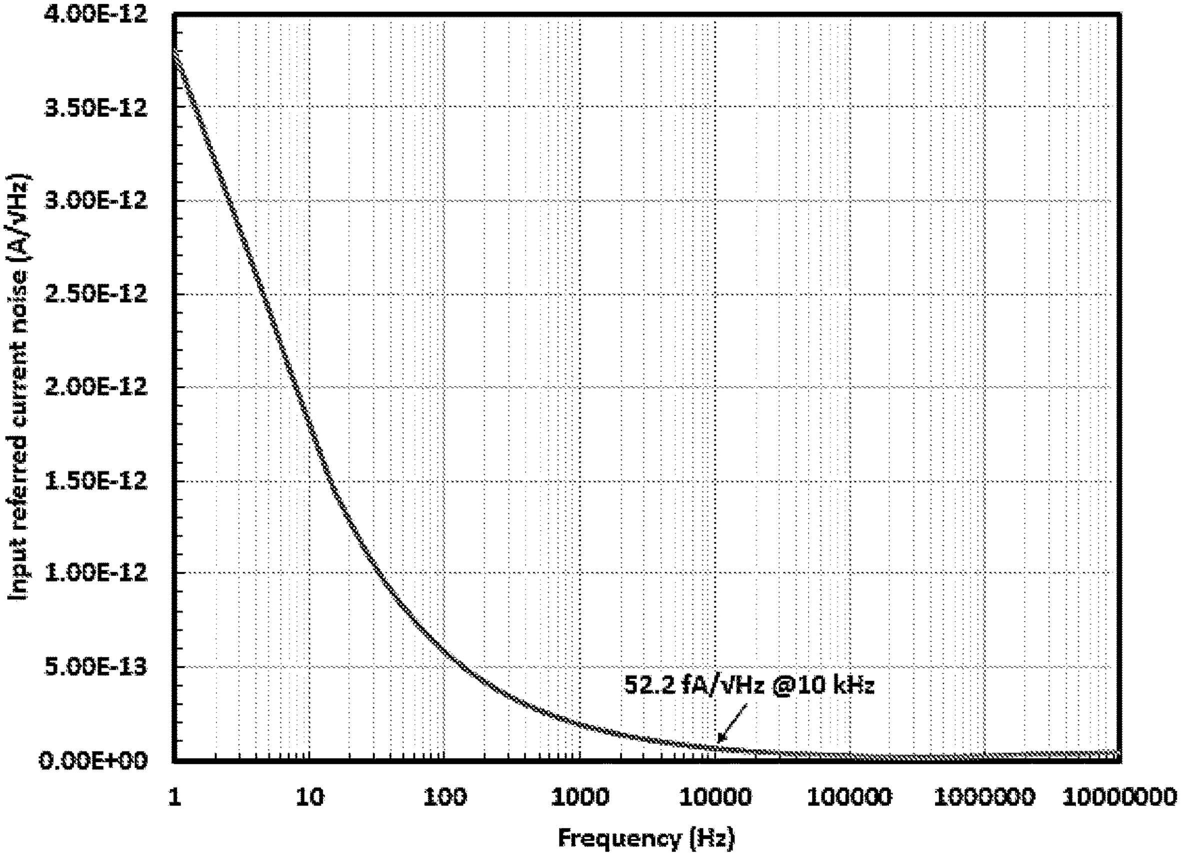

FIG. 11 shows an input-referred noise current response of the difference-differential telescopic cascode amplifier of FIG. 7.

DETAILED DESCRIPTION

In accordance with the present disclosure, embodiments of a glucose sensing method and a glucose sensor system with a CMOS-based low-power, low-noise potentiostat circuit and an electrospun-nanofibrous-membrane (ENFM)-based amperometric glucose sensor on a single silicon chip are presented. In one embodiment, the glucose sensor can detect electrochemical current ranging from 200 nA to 20 μA from a working electrode with a high degree of linearity and the current depends on glucose concentration in the blood. Accordingly, a value of the glucose concentration in the blood can be determined or calculated from a measured current flow in the working electrode.

An exemplary potentiostat, in accordance with embodiments of the present disclosure, includes both a voltage control unit (VCU) and a transimpedance amplifier (TIA), where both VCU and TIA are implemented using a difference-differential telescopic cascode common source amplifier configuration. This type of configuration achieves low-noise, high gain, and stability with significantly lower-power compared to existing potentiostats.

Accordingly, in one embodiment, the present disclosure presents a low-voltage, low-noise, low-power and highly integrated 180 nm CMOS potentiostat with a miniaturized electrospun-nanofibrous-membrane (ENFM)-based amperometric glucose sensor on a single chip. Simulation results confirm the circuit operation with a low supply voltage of 1.4 V and demonstrate a power consumption of 225 μW.

An exemplary potentiostat sensing system, in accordance with embodiments of the present disclosure, achieves competitive performance in terms of low-noise, high gain and increased linearity & stability with a significantly lower-power compared to prior state-of-the-art potentiostats. As shown in FIGS. 1A-1F, an exemplary CMOS-based potentiostat circuit (VCU and TIA) has the potential to be equipped with an ENFM-based glucose sensor and be integrated with an analog to digital converter (ADC) and a digital signal processing circuit for development of a compact and portable device in the form of a glucose sensor system on a silicon chip.

In general, the fabrication of an electrospun conducting polymer of a PEDOT:PSS nanofiber-based glucose sensor involves the following process steps, which are represented in FIGS. 2A-2D (corresponding to the glucose sensor of FIGS. 1A-1C) for an exemplary first approach and FIGS. 2E-2H (corresponding to the glucose sensor of FIGS. 1D-1F) for an exemplary second approach, among others.

Approach 1

Figure 2A:
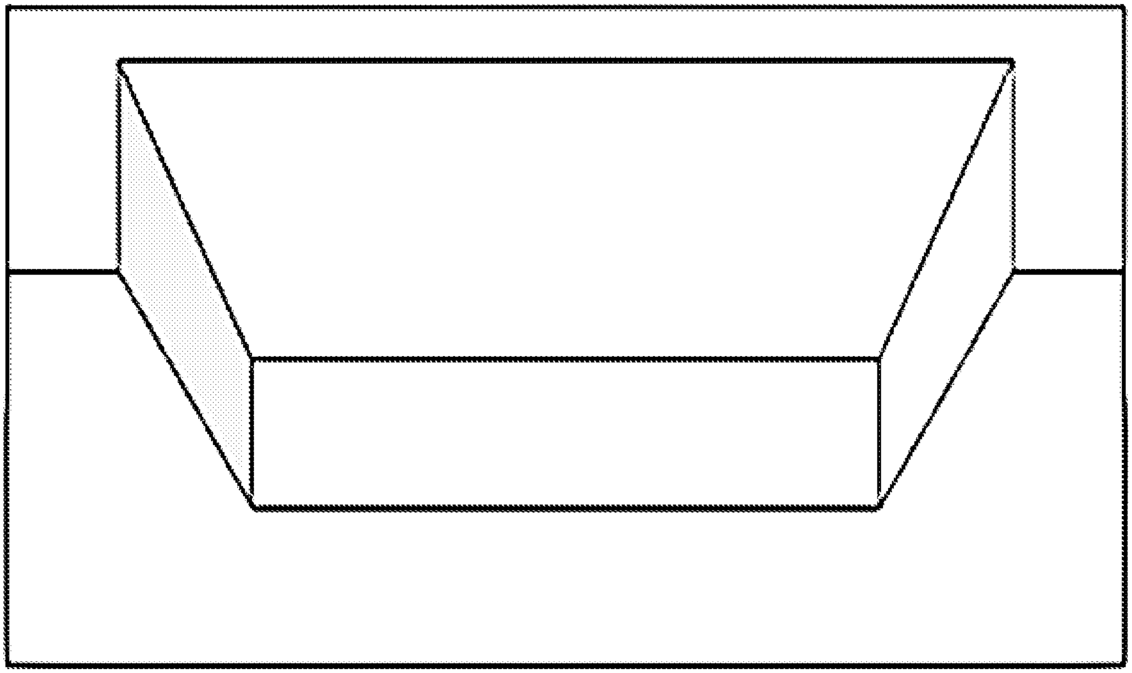
Figure 2B:
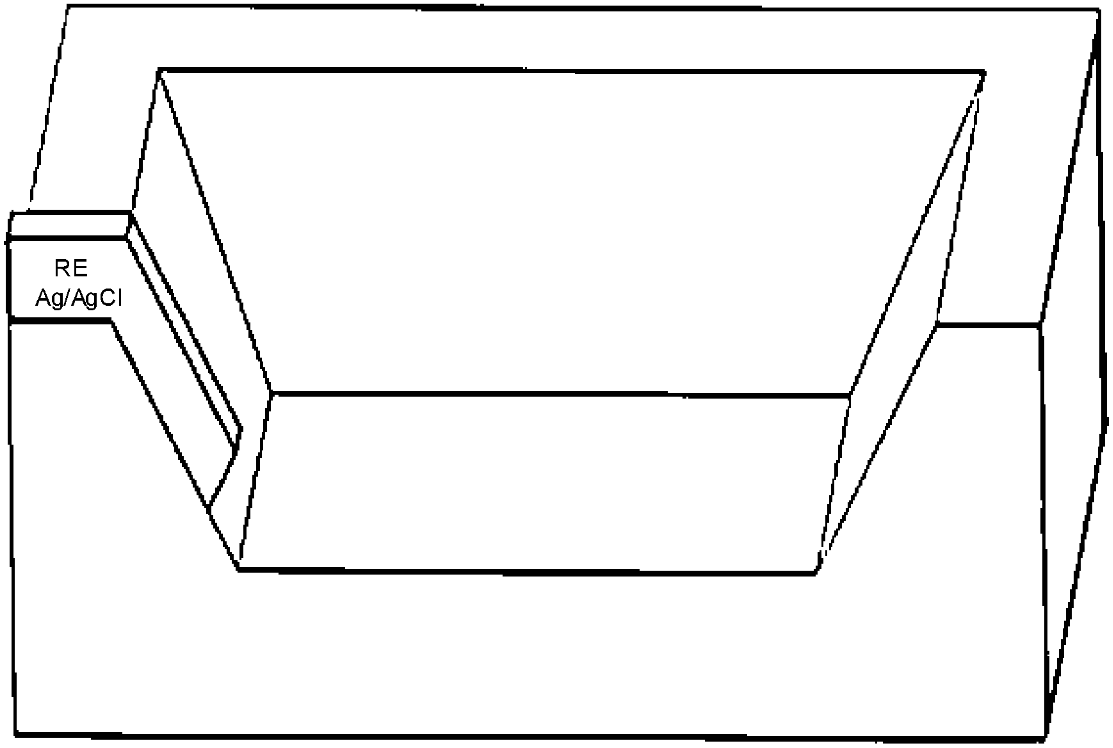
Figure 2C:
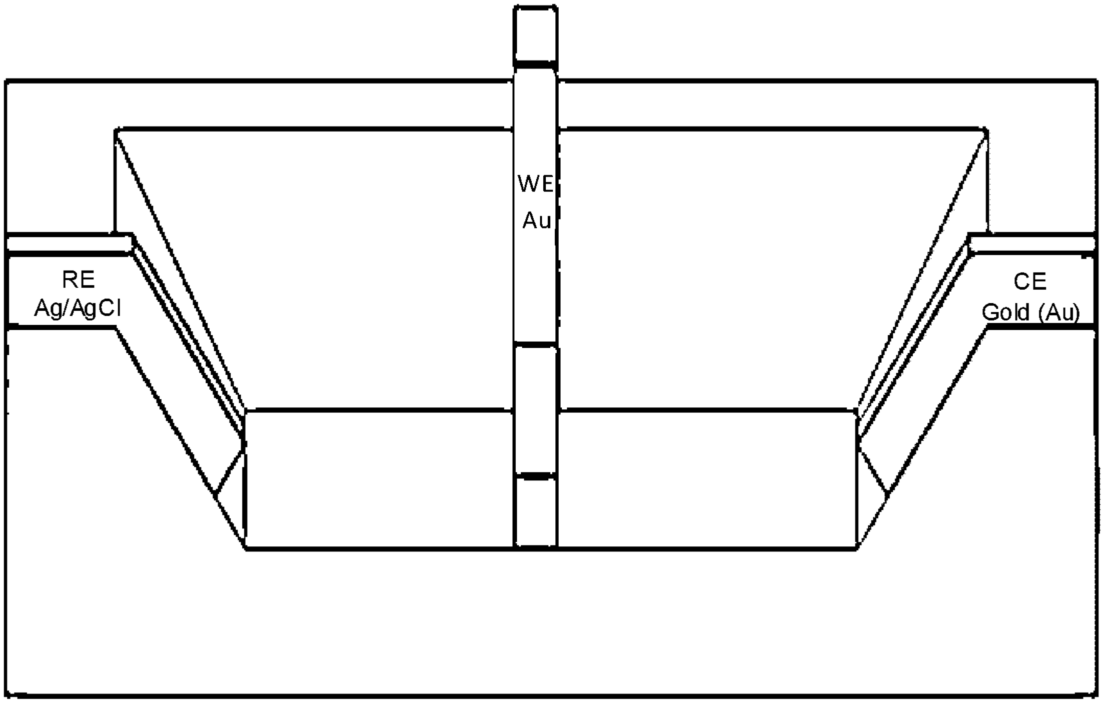
Figure 2D:
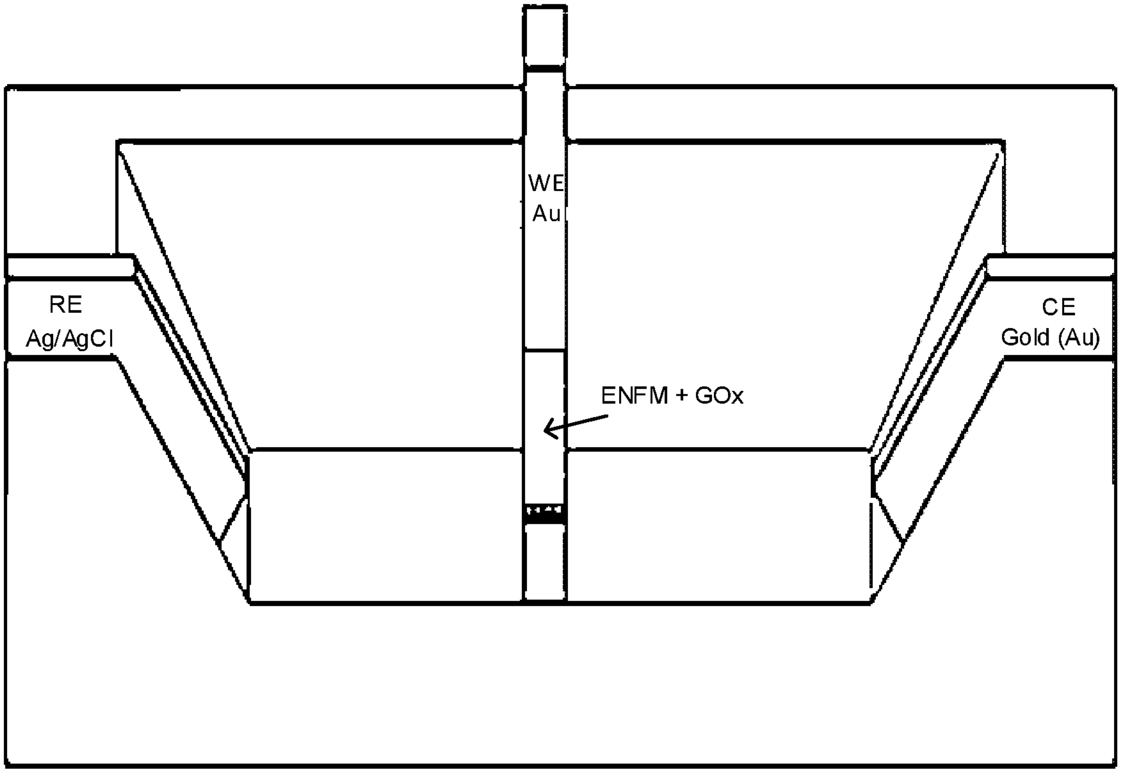

As shown in FIG. 2A, a silicon substrate is cleaned with acetone, methanol followed by plasma cleaning. Then, silicon dioxide ($SiO_2$) layer is grown through oxidation on the top layer of the silicon wafer. The top part of the silicon wafer is patterned using a photolithography process with a mask. Next, the patterns are transferred onto the substrate after the development of patterns according to the mask. The wafer is etched using buffered HF (BHF) to remove the exposed part of the $SiO_2$ layer. The cavity is anisotropic etched in KOH etching, and the RIE etching is carried out to remove the $SiO_2$ layer. Next, a reference electrode region is patterned by photolithography and the sputtered silver/silver chloride (Ag/AgCl) layer is etched and stripped to form a reference electrode, as indicated in FIG. 2B. The counter electrode (CE) and the working electrode (WE) region are patterned by photolithography. Then, the sputtered gold layer is etched and stripped to form CE and WE electrodes, as shown in FIG. 2C. The electrospinning solution is prepared by dissolving 1.18 g of polyvinylidene fluoride (PVDF) and 0.22 g of PEDOT:PSS in 2 ml of tetrahydrofuran (THF) and stirring for 1 hour at 60° C. The prepared solution is electrospun with the applied voltage of 18 kV, a flow rate of 10 μL $min^{-1}$, and the distance from the collector plate to the tip is 29 cm at which the fibers start spinning on to the collector plate and the fibrous layer is placed on to the WE. As shown in FIG. 2D, after drying the ENFM electrode at 60° C. for 4 hours; a glucose oxidase ($GO_x$) enzyme solution is drop casted onto the nanofibrous layer. Then, for immobilization of the enzyme onto the nanofibrous membrane, the ENFM electrodes are kept at 4° C. for 24 hours.

Approach 2

Figure 2E:
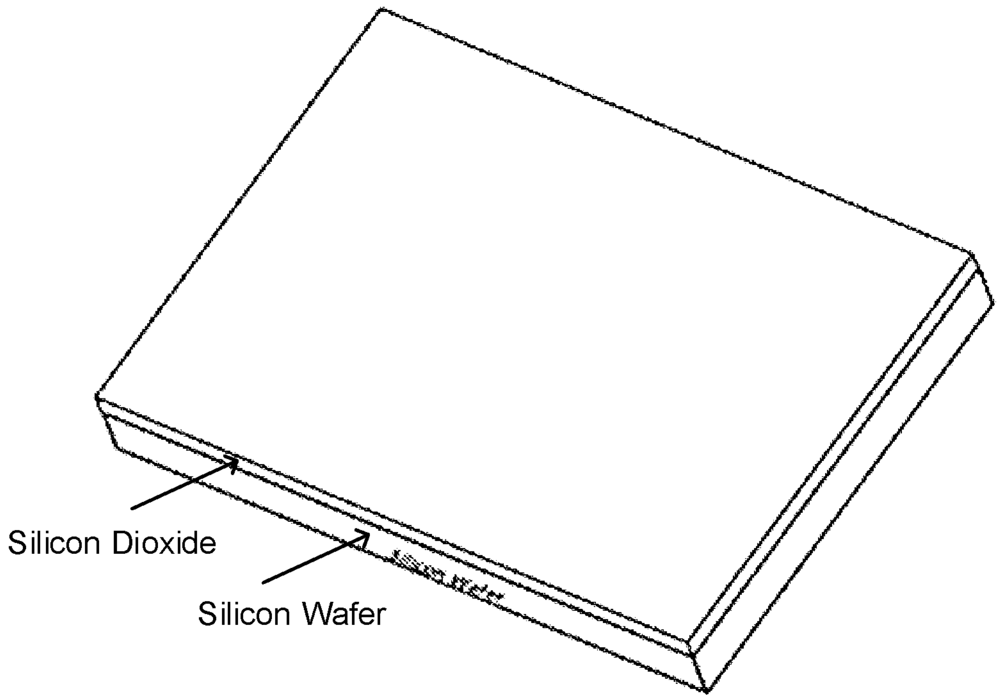
Figure 2F:
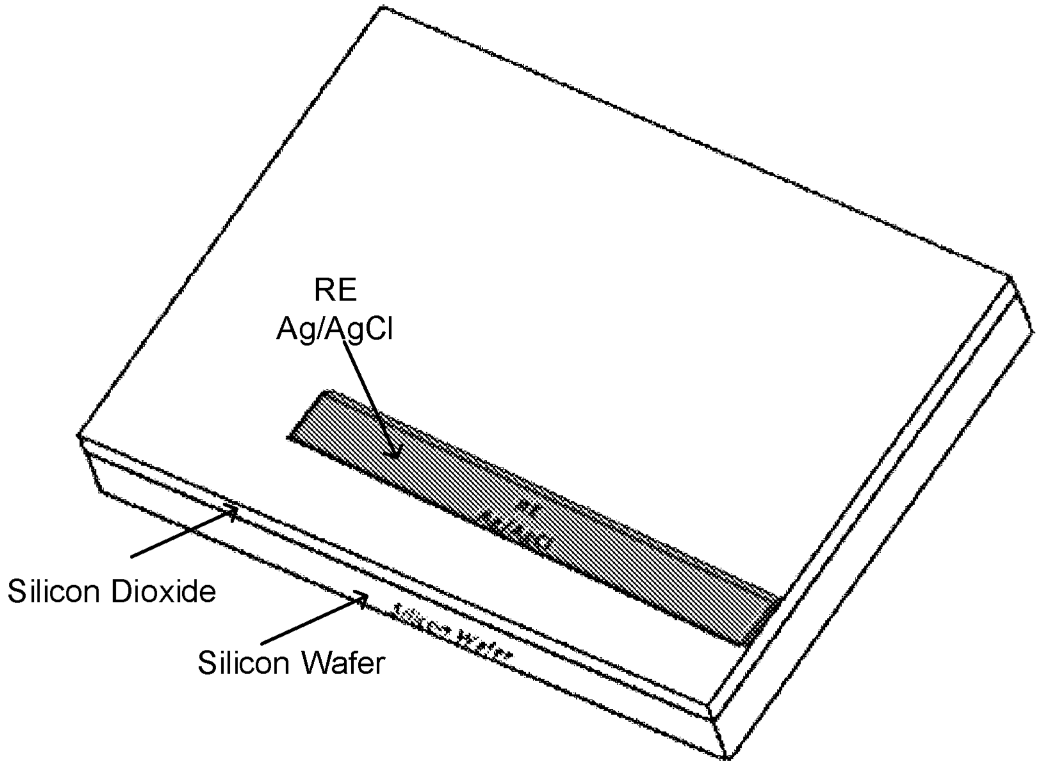

In an additional embodiment, the fabrication of an electrospun conducting polymer of PEDOT:PSS nanofiber based glucose sensor involves the following process steps, which are represented in FIGS. 2E-2H. As shown in FIG. 2E, a silicon substrate is cleaned with acetone, methanol followed by plasma cleaning. Then, a silicon dioxide ($SiO_2$) layer is grown through oxidation on the top layer of the silicon wafer. The RE region is patterned on the top part of the silicon wafer using a photolithography process with a mask, an Ag/AgCl layer is sputtered, and the photoresist is stripped to form a reference electrode, as indicated in FIG. 2F.

Figure 2G:
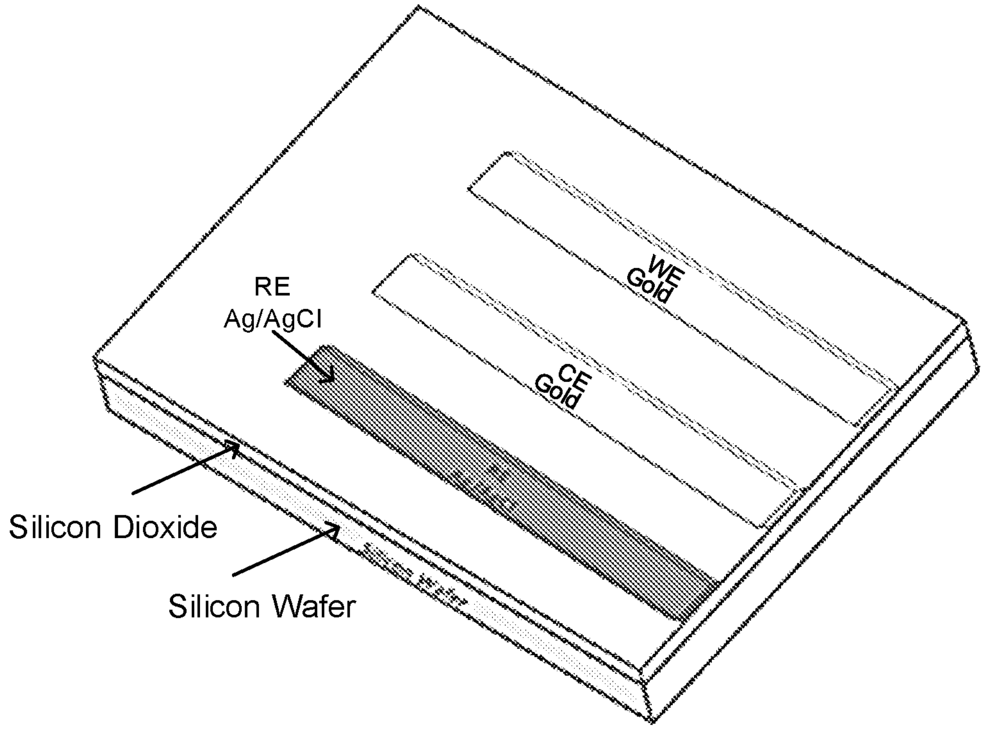
Figure 2H:
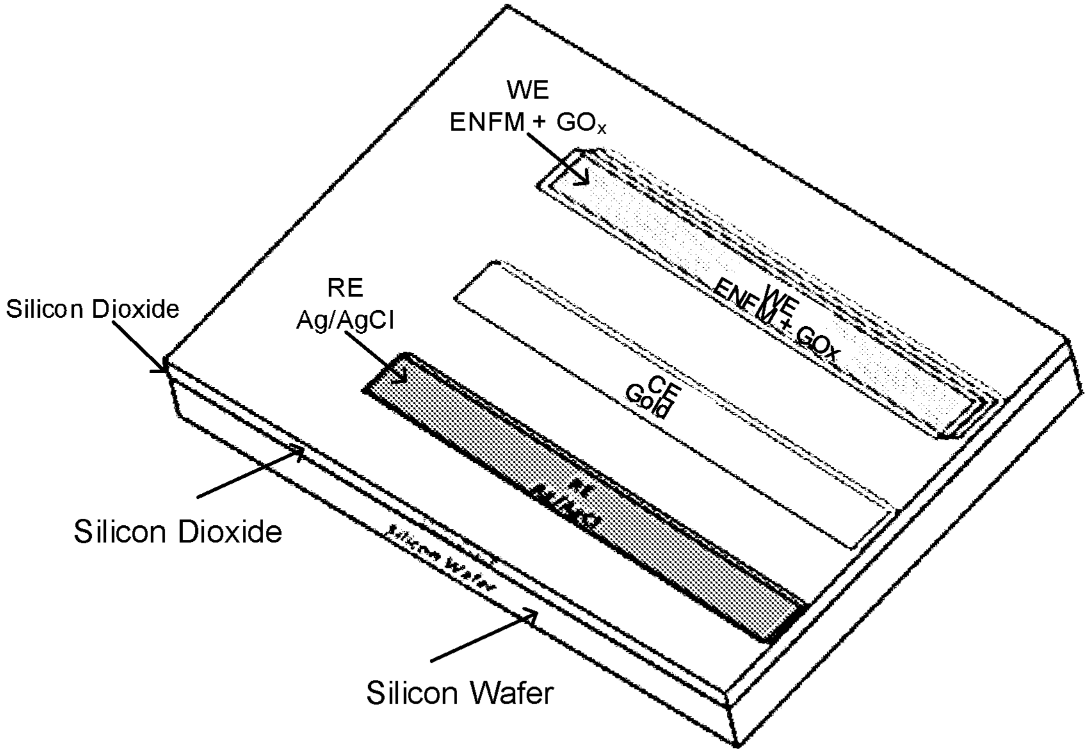

The counter electrode (CE) and the working electrode (WE) regions are patterned by photolithography and the sputtered gold layer is etched. Then, the photoresist is stripped to form CE and WE electrodes, as shown in FIG. 2G. The electrospinning solution is prepared by dissolving 1.18 g of polyvinylidene fluoride (PVDF) and 0.22 g of PEDOT:PSS in 2 mL of tetrahydrofuran (THF) and stirring for 1 hour at 60° C. The prepared solution is electrospun with an applied voltage of 18 kV and a flow rate of 10 μL $min^{-1}$ with the distance from the collector plate to the tip being 29 cm. Next, the fibers start spinning on to the collector plate and the fibrous layer is placed on to the WE. As shown in FIG. 2H, after drying the ENFM electrode at 60° C. for 4 hours, a glucose oxidase enzyme solution is drop casted onto the nanofibrous layer. For immobilization of an enzyme onto the nanofibrous membrane, the ENFM electrodes are kept at 4° C. for 24 hours.

Figure 3A:
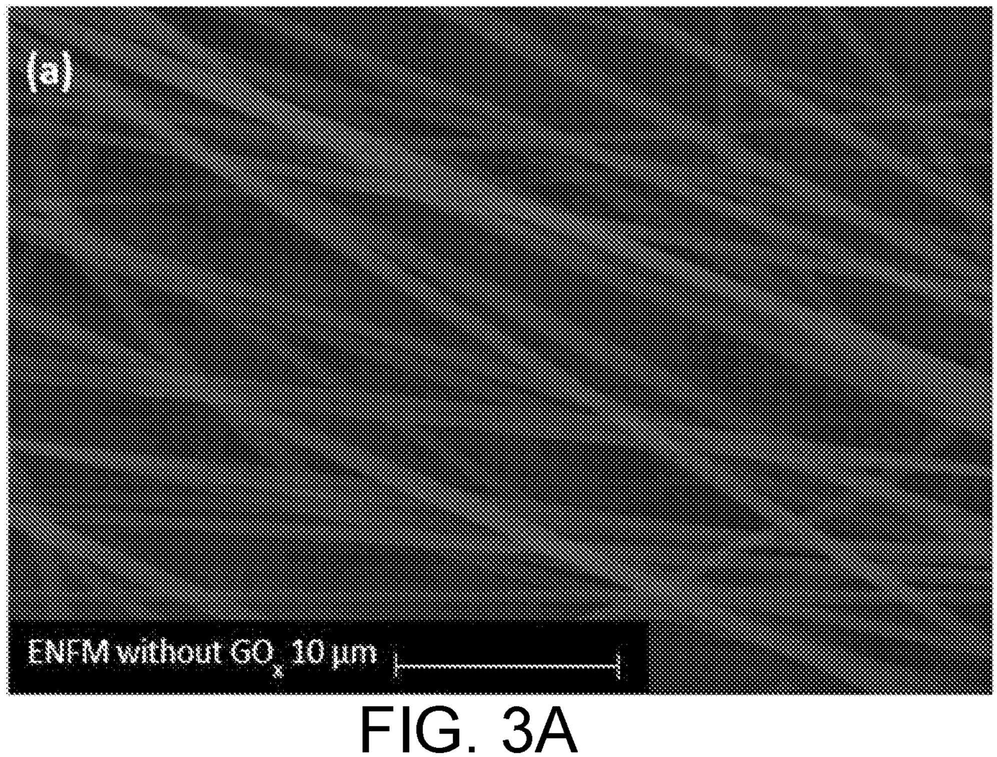
Figure 3B:
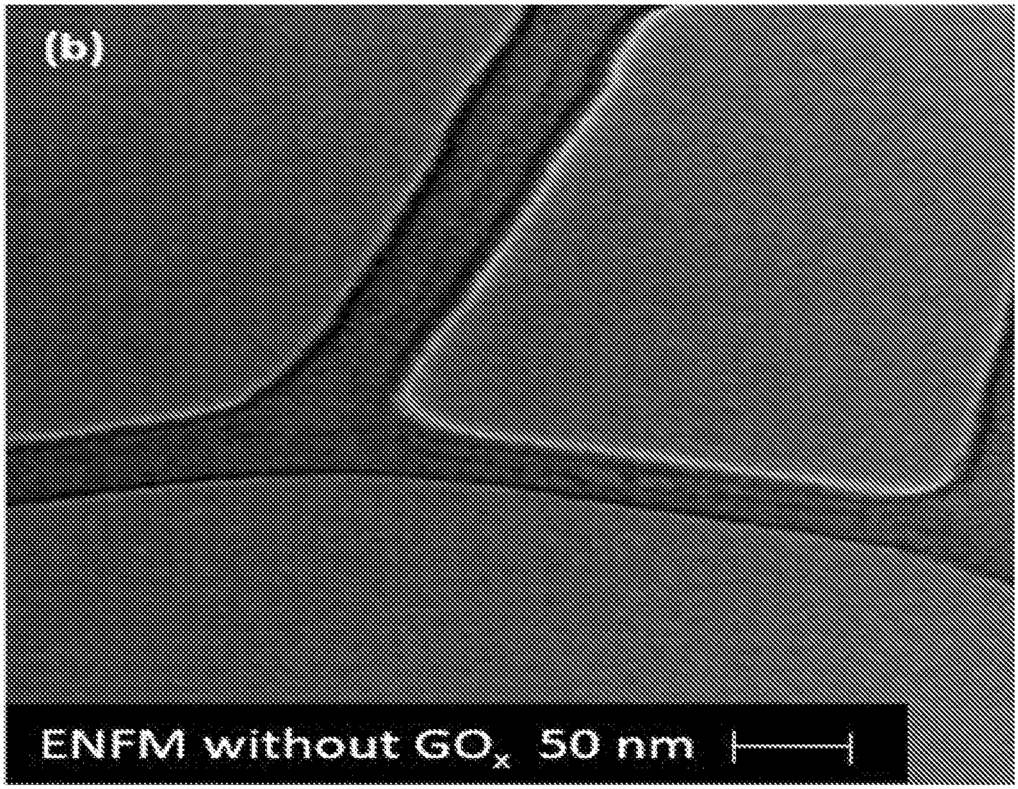
Figure 3C:
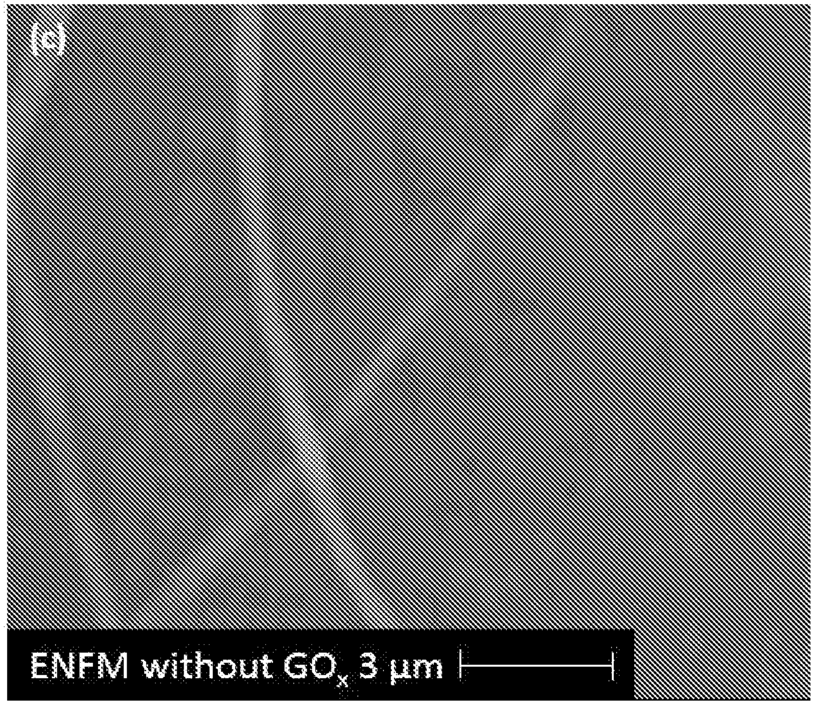
Figure 3D:
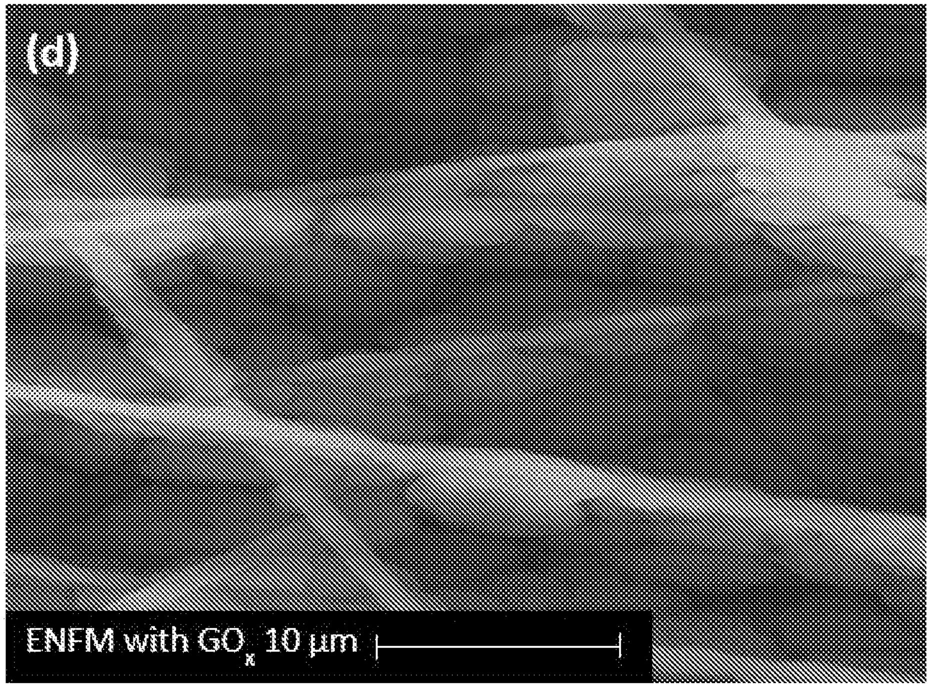
Figure 3E:
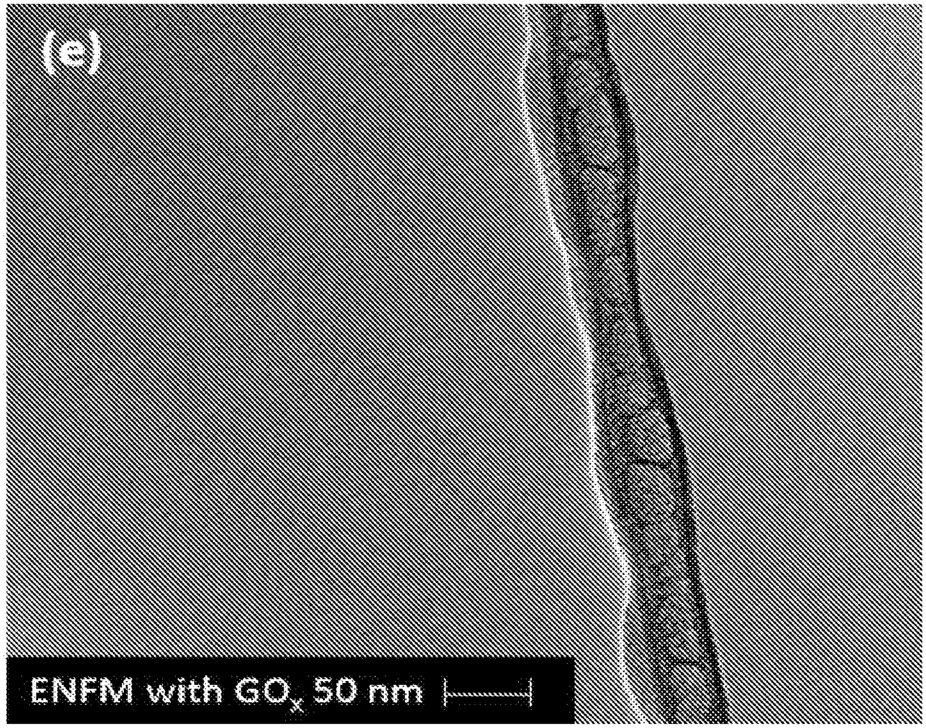

Scanning electron microscope (SEM), transmission electron microscope (TEM), and atomic force microscope (AFM) (tapping mode) pictures of the fabricated polymer-based ENFM are shown in FIGS. 3A-3E. In particular, FIGS. 3A & 3D show the SEM images, FIGS. 3B & 3E show the TEM images, and FIGS. 3C & 3E show the AFM images. The morphology and a randomly oriented fibrous structure with a diameter in the range of 25-50 nm are shown in these images.

Figure 3F:
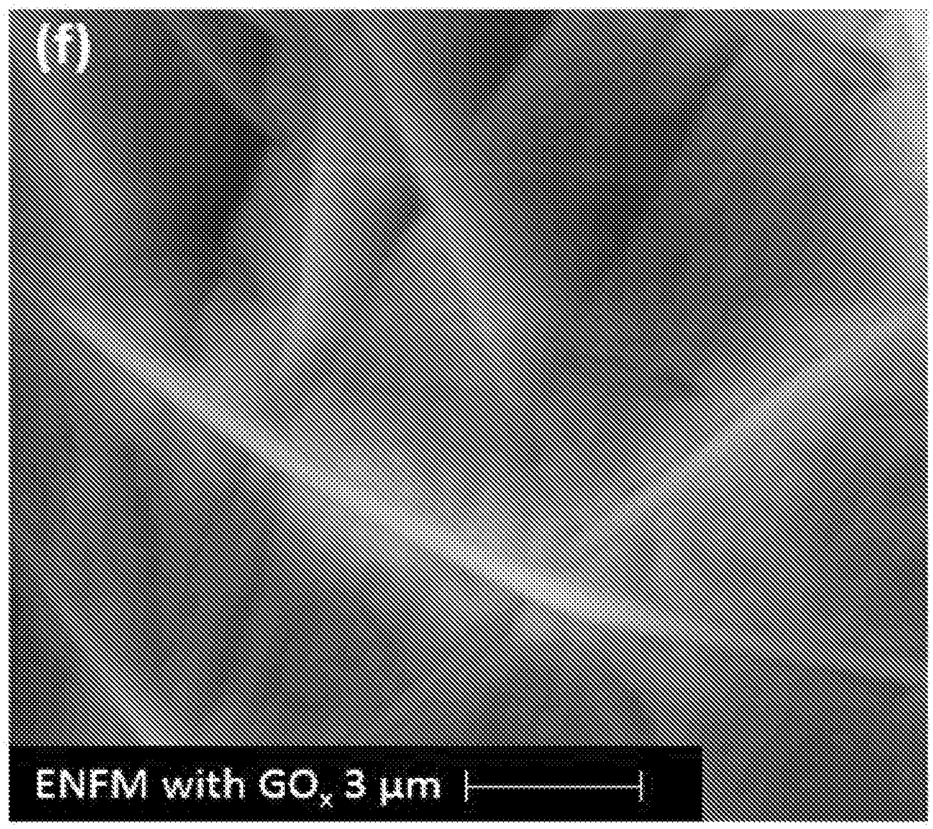

FIGS. 3D-3F show a surface coverage of closely packed mesh-like structures, which facilitate higher $GO_x$ populous on the nanofibrous matrix and capitalize on the larger surface area. In turn, this helps in binding the $GO_x$ enzyme within the fibrous membrane of the WE electrode when placed in an electrolyte solution and improves the sensitivity, stability, repeatability and durability of the sensing electrode (WE).

During testing, electrochemical measurements were performed on VersaSTAT-4 by Princeton Applied Research (PAR) with the three-electrode test setup with the ENFM electrode of surface area 0.35 cm×0.5 cm as the working electrode (WE), Ag/AgCl as the reference electrode (RE), and a bare gold electrode as the counter electrode (CE). The electrocatalytic activity of the working electrode was evaluated using chronoamperometry for various glucose concentrations and the current response was recorded for 160 seconds, as shown in FIG. 4. The limit of detection was calculated as 3*standard deviation (0.0014 μA) divided by the slope (1.7885 μA/mM) which is equal to 2.3 μM and sensitivity was calculated as slope of the calibration curve (1.7885 μA/mM) divided by the total surface area of the ENFM electrode (0.35 cm×0.5 cm) which is equal to 10.22 μA/mM $cm^2$. The ENFM working electrode demonstrates a response time of less than 4 seconds for glucose detection.

Next, the electrochemical impedance spectroscopy (EIS) measurements were performed for an exemplary ENFM-based glucose sensing electrode. Accordingly, a Nyquist plot and an equivalent circuit model of the ENFM electrode were analyzed in 5 mM of electrolyte (potassium ferricyanide+glucose) solution within a frequency range of 100 mHz-10 KHz at an amplitude of 10 mV, as shown in FIG. 5. The equivalent electrical circuit model of the ENFM-based glucose sensing electrode was generated by utilizing an EIS spectrum analyzer. The electrochemical setup with the ENFM electrode was modeled using a series-parallel combination of the resistor-capacitor (RC) network which includes a double-layer capacitance ($C_{WE}$) of 4.5 μF, solution resistance ($R_s$) of 200Ω, a charge transfer or polarization resistance ($R_{WE}$) of 34.3Ω, and a Warburg impedance ($W_{WE}$) of 367.9. The large double-layer capacitance and the Warburg impedance represent a large surface area due to the porosity of the nanofibrous membrane. The Nyquist plot of imaginary part Im(Z)=Z" of the total impedance versus real part of the impedance Re(Z)=Z' is a depressed semicircle which is equivalent to $R_{WE}$ at high frequencies and the well-defined linear Warbourg diffusive features are present at lower frequencies for the ENFM electrode. Based on the glucose concentrations, the electrochemical current can be as small as nanoamps to microamps. This requires a highly sensitive, low-noise current measuring circuitry, which can be accomplished by using an exemplary complementary-metaloxide-semiconductor (CMOS)-based difference-differential telescopic cascode TIA in accordance with the present disclosure.

The potentiostat circuit connected to the electrochemical cell utilizes a three electrode system which includes an RE, CE, and WE for amperometric measurements, in accordance with embodiments of the present disclosure. While a consistent potential is maintained between the working (WE) and the reference (RE) electrodes, an electrochemical reaction happens at the WE which is functionalized with the enzyme, in which the CE provides a path for the sensing current to the grounded WE and the current through the cell is controlled by the VCU so that the reference electrode is at the fixed potential throughout the reaction.

Accordingly, FIG. 6 shows a pictorial representation of an embodiment of an exemplary potentiostat circuit design with an ENFM-based glucose sensor having the WE as an ENFM-based sensing electrode, RE as an Ag/AgCl electrode, and CE as a gold-coated electrode. The potentiostat circuit has both a VCU and an electrochemical current measuring/current to voltage converter unit (e.g., a TIA device). In one embodiment, the CMOS-based potentiostat circuit can be implemented using a difference-differential telescopic cascode amplifier configuration.

For example, an exemplary difference-differential telescopic cascode TIA circuit is represented in FIG. 7, in accordance with the present disclosure. Here, transistors can be made to operate in a saturation region to get the maximum gain. The bias circuit can be designed using a current mirror technique to minimize the effect of channel length modulation in which the sizes of the current mirrors and the cascode amplifier are the same. The resistors $R_1$, $R_2$, $R_4$, $R_5$, and $R_f$ can be implemented using poly resistors and $C_c$ is the coupling capacitor which can be implemented using a metal-insulator-metal capacitor (MIMCAP) device by gpdk180 nm CMOS library.

The difference-differential telescopic cascode TIA amplifies the difference between two signals and rejects any common signals to the two input terminals ($I_{in1}$ and $I_{in2}$). The circuit is shown with inputs $I_{in1}$ and $I_{in2}$. To analyze the circuit, we will use superposition and virtual short concepts. Accordingly, if the input $I_{in2}$=0, then there is no current in $R_4$ and $R_5$; therefore $V_{2a}$=0. The resulting circuit acts as an inverting amplifier.

$$\nabla_{o1} = -\frac{R_f}{R_2} I_{in1} \tag{1}$$

If the input $I_{in1}$=0, $R_4$ and $R_5$ form a voltage divider, since the current into the amplifier is zero. Therefore, $$V_{2a} = \frac{R_5}{R_4 + R_5} I_{in2} \tag{2}$$

From the virtual short concept, $V_{1a}$=$V_{2a}$ and the circuit becomes a non-inverting amplifier, for which $$V_{o2} = \left(1 + \frac{R_f}{R_2}\right) V_{1a} = \left(1 + \frac{R_f}{R_2}\right) V_{2a} \tag{3}$$

Substituting Equation (2) into Equation (3), we obtain Equation (4):

$$V_{o2} = \left(1 + \frac{R_f}{R_2}\right)\left(\frac{R_5}{R_4 + R_5}\right) I_{in2} \tag{4}$$

Since the net output voltage is the sum of individual terms, $$V_o = V_{o1} + V_{o2} \tag{5}$$

$$V_o = \left(1 + \frac{R_f}{R_2}\right)\left(\frac{R_5}{R_4 + R_5}\right)I_{in2} - \left(\frac{R_f}{R_2}\right)I_{in1} \tag{6}$$

If $$\frac{R_5}{R_4} = \frac{R_f}{R_2},\ I_{in1}\ \&\ I_{in2} \approx I_{cell}$$

is the current across the resistor $R_1$, and $R_1 << R_f$ and $R_2$, then $$V_o = \frac{R_f}{R_2} R_1 I_{cell} \tag{7}$$

Next, a small signal analysis is performed on the differential telescopic cascode configuration of FIG. 7, the cascode load is replaced by a cascode current source load, and the coupling capacitor $C_c$ is used to improve the stability of the amplifier. FIG. 8 shows the small signal analysis of the differential telescopic cascode amplifier and its small-signal output resistance $R_{out}$ can be found using Equation (8).

$$R_{out2} = [(g_{m3,4} r_{ds3,4} + 1) r_{ds1,2} + r_{k3,4}] \| [(g_{m7,8} r_{ds7,8} + 1) r_{ds5,6} + r_{ds7,8})] \tag{8}$$

$$R_{out2} = (g_{m3,4} r_{sa3,4} r_{ds1,2}) \| (g_{m7,8} r_{ds7,8} r_{ds5,6})$$

The open loop gain can be calculated from differential inputs ($V_{in1} - V_{in2}$) to the single-ended output $V_2$, as shown in Equation (9):

$$A_{V2} = \frac{V_2}{V_{in1} - V_{in2}} = \left(-g_{m1,2} \frac{g_{m3,4} g_{m7,8} r_{ds1,2} r_{ds3,4} r_{ds7,8} r_{ds5,6}}{g_{m3,4} r_{ds3,4} r_{ds1,2} + g_{m7,8} r_{ds7,8} r_{ds5,6}}\right) \tag{9}$$

To find the total gain of the amplifier from $V_{in}$ to $V_{out}$, we need to consider a common source amplifier and the source follower gain. The common source amplifier gain is given in Equation (11) and source follower gain is given in Equation (12).

$$A_{V3} = -g_{m9}(r_{ds9} \| r_{ds10}) \tag{10}$$

-continued $$A_{V3} = \frac{V_{out}}{V_2} = \left(-g_{m9} \frac{r_{ds9}, r_{ds10}}{r_{ds9} + r_{ds10}}\right) \tag{11}$$

$$A_{V4} = \frac{V_{out}}{V_3} \leq 1 \tag{12}$$

If we substitute Equation (9), (11) and (12) in Equation (13) below, the total open loop gain of the differential telescopic cascode amplifier becomes:

$$A_V = A_{V2} \cdot A_{V3} \cdot A_{V4} = \frac{\nabla_{out}}{\nabla_{in}} = \left(-g_{m1,2} \frac{g_{m3,4} g_{m7,8} r_{ds1,2} r_{ds3,4} r_{ds7,8} r_{ds5,6}}{g_{m3,4} r_{ds3,4} r_{ds1,2} + g_{m7,8} r_{ds7,8} r_{ds5,6}}\right)\left(-g_{m9} \frac{r_{ds9} \cdot r_{ds10}}{r_{ds9} + r_{ds10}}\right) \tag{13}$$

Let's consider the noise analysis of an exemplary differential telescopic cascode amplifier, as shown in FIG. 9. The primary noise sources of the amplifier are $N_1$-$N_2$, $N_5$-$N_6$, $N_9$-$N_{10}$ and $N_{14}$-$N_{13}$. The input-referred noise voltage per unit bandwidth is given by both the thermal noise and flicker noise and is expressed in Equation (14):

$$\overline{V_{n,in}^2} = \underbrace{4kT\left(2\frac{2}{3g_{m1,2}} + 2\frac{2g_{m5,6}}{3g_{m1,2}^2} + \frac{2}{3g_{m9}} + \frac{2g_{m10}}{3g_{m9}^2} + \frac{2}{3g_{m14}} + \frac{2g_{m13}}{3g_{m14}^2}\right)}_{Thermalnoise} + \tag{14}$$

$$2\frac{K_N}{C_{ox}(W \cdot L)_{1,2}} \cdot \frac{1}{f} + 2\frac{K_P}{C_{ox}(W \cdot L)_{5,6}} \cdot \frac{1}{f} \cdot \frac{g_{m5,6}^2}{g_{m1,2}^2} +$$

$$\underbrace{\frac{K_P}{C_{ox}(W \cdot L)_9} \cdot \frac{1}{f} + \frac{K_N}{C_{ox}(W \cdot L)_{10}} \cdot \frac{1}{f}\frac{g_{m10}^2}{g_{m9}^2} + \frac{K_P}{C_{ox}(W \cdot L)_{14}} \cdot \frac{1}{f} + \frac{K_N}{C_{ox}(W \cdot L)_{13}} \cdot \frac{1}{f}\frac{g_{m13}^2}{g_{m14}^2}}_{Flickernoise}$$

where $K_N$ and $K_P$ denote the 1/f noise coefficients of NMOS and PMOS transistors, f is the frequency, $g_m$ is the transconductance, W and L are the channel width and length of MOS transistors, $C_{ox}$ is the gate capacitance.

The differential telescopic cascode amplifier input-referred voltage noise can be minimized by increasing the transconductance $g_m$ of transistors. When the transistor operates in saturation region, the equation for $g_m$ is given as follows:

$$g_m = \sqrt{2\mu_o C_{ox} I_D \frac{W}{L}} \tag{15}$$

To minimize the input-referred voltage noise, $g_m$ should be higher by making transistor wider which results in the smallest noise.

The VCU utilizes a high gain amplifier to maintain a constant voltage difference by regulating the current, and the TIA has a low-noise and high gain to satisfy the output voltage swing for the maximum electrochemical current of 20 μA.

In accordance with embodiments of the present disclosure, the VCU and TIA in the potentiostat are designed using a differential telescopic cascode amplifier topology, which has a 92 dB open loop gain and 77° phase margin with approximately 10 KHz bandwidth.

Next, FIGS. 10A and 10B show the simulated open loop gain and phase responses, and FIG. 11 shows the input-referred noise current response of the difference-differential telescopic cascode amplifier of FIG. 7. In FIG. 11, the input-referred noise current response was 52.2 fA/√Hz at 10 KHz, and the total power consumption of the exemplary potentiostat was 225 W from a single supply voltage of 1.4 V. Additionally, Table I (below) depicts a comparative study of previously reported CMOS-based potentiostats. From Table I, it is observed that an exemplary potentiostat circuit in accordance with the present disclosure has a significant improvement in performance showing low noise, better gain, and less-power dissipation, compared to conventional CMOS-based potentiostats.

TABLE I (COMPARISON OF CMOS-BASED POTENTIOSTAT PERFORMANCE WITH PRIOR STATE-OF-THE-ART POTENTIOSTATS)

| Applications | Biosensor | Biosensor | Biosensor | Biosensor | Biosensor | Biosensor | Gas sensor | Exemplary Potentiostat Biosensor |
|---|---|---|---|---|---|---|---|---|
| Technology | CMOS 350 nm | CMOS 350 nm | CMOS 350 nm | CMOS 350 nm | CMOS 0.5 µm | CMOS 180 nm | CMOS 0.5 µm | CMOS 180 nm |
| Sensing Electrode | ISFET | Micro needle | Pt-nanoS | 3D gold | Nanopore | MEA | RTIL arrays | ENFM |
| Input Current Range | −100 µA-100 µA | 5 µA-30 µA | −20 µA-20 µA | 24 pA-0.35 µA | −10 pA-10 pA | 200 pA-50 nA | 127 nA-16 µA | 200 nA-20 µA |
| Power Consumption | 9.9 mW | 5.1 mW | 9.3 mW | 0.188 mW | 380 µW | 3.21 mW | 241 µW | 225 W |
| Supply Voltage | 3.3 V | 1.65 V | 3.3 V | 3.3V | 3.3 V | 1.8 V | 5 V | 1.4 V |
| Input Referred Noise Current | 150 pA/√Hz | 0.14 µA/√Hz | 0.47 pA/√Hz | 3.1 pA/√Hz | 3 pA/√Hz | 0.48 pA/√Hz | 3.1 pA/√Hz | 52.2 fA/√Hz |

In accordance with various embodiments of the present disclosure, a CMOS potentiostat circuit has been integrated with an ENFM-based amperometric glucose sensor on a single chip. Such a fully integrated CMOS-based potentiostat demonstrates improved performance in terms of low-voltage, low-noise, low-power consumption, high-gain, and miniaturized design. In one embodiment, an exemplary potentiostat includes both VCU and TIA which are designed using difference-differential telescopic cascode amplifier configuration and has been shown to consume 225 µW of power from a 1.4 V voltage supply. Such a difference-differential telescopic cascode amplifier shows a high gain of 92 dB, a better phase margin of 77° with a bandwidth of approximately 10 KHz, and an input-referred noise current of 52.2 fA/√Hz. In one embodiment, a fabricated enzyme immobilized ENFM-based sensing electrode demonstrates the limit of detection (LOD) of 2.3 µM and sensitivity of 10.22 µA/mM $cm^2$ in a glucose solution and it can be reused for up to 50 days. These results provide the basis for utilizing this exemplary low-noise and low-power potentiostat circuit design for integrated biosensing applications, including glucose sensor systems and related methods.

It should be emphasized that the above-described embodiments of the present disclosure are merely possible examples of implementations, merely set forth for a clear understanding of the principles of the disclosure. Many variations and modifications may be made to the above-described embodiment(s) without departing substantially from the principles of the disclosure. All such modifications and variations are intended to be included herein within the scope of this disclosure and protected by the following claims.

The invention claimed is:

1. A method for forming a glucose sensor, comprising:

providing a silicon chip comprising an integrated potentiostat circuit, wherein the potentiostat circuit comprises a voltage control unit and a transimpedance amplifier; and integrating a nanofibrous-membrane-based amperometric glucose sensor on the silicon chip, wherein:

the glucose sensor comprises a working electrode, a reference electrode, and a counter electrode, wherein the working electrode comprises a nanofibrous-membrane comprising glucose oxidase bound to nanofibers;

the potentiostat circuit is coupled to the glucose sensor;

the voltage control unit controls a voltage difference between the working electrode and the reference electrode; and the transimpedance amplifier measures a current flow between the working electrode and the counter electrode, wherein a strength of the current flow corresponds to an amount of glucose present in a sample of blood on the glucose sensor.

2. The method of claim 1, wherein the potentiostat circuit is implemented using a difference-differential telescopic cascode common source amplifier configuration.

3. The method of claim 1, wherein the provided silicon chip further comprises an analog to digital converter and a digital signal processing circuit integrated on the silicon chip.

4. The method of claim 1, wherein the reference electrode comprises an Ag/AgCl electrode and the counter electrode comprises a gold-coated electrode.

5. The method of claim 1, wherein the nanofibrous-membrane comprises an electrospun-nanofibrous-membrane (ENFM).

6. The method of claim 1, wherein the nanofibrous-membrane comprises PEDOT:PSS nanofibers.

7. The method of claim 1, wherein the potentiostat circuit is configured to detect an electrochemical current in the range of 200 nA to 20 µA from the working electrode.

8. The method of claim 1, wherein the potentiostat circuit is characterized by a power consumption of 225 µW.

9. The method of claim 7, wherein the potentiostat circuit is characterized by a power consumption of 225 μW.

10. A method for forming a glucose sensor, comprising:

providing a silicon chip comprising an integrated potentiostat circuit, wherein the potentiostat circuit comprises a voltage control unit and a transimpedance amplifier; and forming a nanofibrous-membrane-based glucose sensor on the silicon chip, comprising:

forming a working electrode, a reference electrode, and a counter electrode on the silicon chip, wherein the working electrode comprises a nanofibrous-membrane comprising glucose oxidase bound to nanofibers; and coupling the potentiostat circuit to the glucose sensor on a single chip, wherein:

the voltage control unit controls a voltage difference between the working electrode and the reference electrode; and the transimpedance amplifier measures a current flow between the working electrode and the counter electrode, wherein a strength of the current flow corresponds to an amount of glucose present in a sample on the glucose sensor.

11. The method of claim 10, wherein the potentiostat circuit is implemented using a difference-differential telescopic cascode common source amplifier configuration.

12. The method of claim 10, wherein the provided silicon chip further comprises an analog to digital converter and a digital signal processing circuit integrated on the silicon chip.

13. The method of claim 10, wherein:

forming the reference electrode comprises forming an Ag/AgCl electrode; and forming the counter electrode comprises forming an electrode comprising gold.

14. The method of claim 10, wherein forming the working electrode comprises:

forming a first electrode comprising gold; and electrospinning an electrospinning solution to form the nanofibers on the first electrode.

15. The method of claim 14, wherein the nanofibers comprise PEDOT:PSS nanofibers.

16. The method of claim 10, wherein the nanofibrous-membrane comprises PEDOT:PSS nanofibers.

17. The method of claim 10, further comprising forming a cavity in the silicon chip, and wherein the working electrode, a reference electrode, and a counter electrode are formed within the cavity.

18. The method of claim 10, wherein the potentiostat circuit is configured to detect an electrochemical current in the range of 200 nA to 20 μA from the working electrode.

19. The method of claim 10, wherein the potentiostat circuit is characterized by a power consumption of 225 μW.

20. The method of claim 18, wherein the potentiostat circuit is characterized by a power consumption of 225 μW.

* * * * *